United States Patent [19]
Blanchard et al.

[11] Patent Number: 5,998,189
[45] Date of Patent: Dec. 7, 1999

[54] POLYPEPTIDE DERIVATIVES OF DOG GASTRIC LIPASE AND PHARMACEUTICAL COMPOSITIONS CONTAINING SAME

[75] Inventors: Claire Blanchard, Grigny; Claude Benicourt, Houilles; Jean-Louis Junien, Sevres, all of France

[73] Assignee: Warner-Lambert Company, Morris Plains, N.J.

[21] Appl. No.: 09/073,674

[22] Filed: May 6, 1998

Related U.S. Application Data

[62] Division of application No. 08/227,108, filed as application No. PCT/FR93/01260, Dec. 16, 1993.

[30] Foreign Application Priority Data

Dec. 16, 1992 [FR] France ................................ 92 15201
Dec. 16, 1993 [FR] France ................. PCT/FR93/01260

[51] Int. Cl.$^6$ ............................. C12N 9/20; A61K 38/46
[52] U.S. Cl. ......................................... 435/198; 424/94.6
[58] Field of Search .............................. 435/198; 424/94.6

[56] References Cited

U.S. PATENT DOCUMENTS 5,075,231  12/1991  Moreau et al. ......................... 435/198

FOREIGN PATENT DOCUMENTS 0261016  3/1988  European Pat. Off. .
3737333  5/1989  Germany .
8601532  3/1986  WIPO .

OTHER PUBLICATIONS

Carriere, F., et al., "Purification and biochemical characterization of dog gastric lipase," *European Journal of Biochemistry*, 1991, vol. 202, pp. 75–83.

Iverson, S.J., et al., "Milk lipid digestion in the neonatal dog; the combined actions of gastric and bile salt stimulated lipases," *Biochemica at Biophysica acta*, 1991, vol. 1083, No. 1, pp. 109–119.

Bodmer, M.W. et al. "Molecular cloning of a human gastric lipase and expression of the enzyme in yeast." Biochimica et Biophysica Acta (Aug. 1987), vol. 909, No. 3, pp. 237–244.

*Primary Examiner*—Charles L. Patterson, Jr.
*Attorney, Agent, or Firm*—Todd M. Crissey

[57] ABSTRACT

The present invention relates to polypeptide derivatives of dog gastric lipase as obtained by genetic engineering as well as to the nucleotide sequence encoding this recombinant DGL. It also relates to the use of this recombinant DGL for the production of pharmaceutical compositions intended especially for the treatment of pathologies linked to the insufficiency, or even the absence, of secretion of lipases in the body of an individual.

6 Claims, 22 Drawing Sheets

| LIPASE | | | 1 | | | | |
|---|---|---|---|---|---|---|---|
| human gastric | Thr | His | Gly | Leu | Phe | Gly | Lys |
| rabbit gastric | Thr | His | Gly | Leu | Phe | Gly | Lys |
| rat lingual | Ala | His | Gly | Leu | Phe | Gly | Lys |
| dog gastric | | | | Leu | Phe | Gly | Lys |

FIG. 1

LIPASE

|  |  |
|---|---|
| human gastric | 94<br>↓<br>CA CAT GGT TTG TTT GGA AAA |
| rabbit gastric | 103<br>↓<br>CA CAT GGT CTT TTT GGA AAA |
| rat lingual | 94<br>↓<br>CA CAT GGC CTA TTT GGA AAA |

5'  GG GCA CAT GGT TTG TTT GGA AAA 3'    (DGL₁)
    ‿‿‿‿‿‿        C   C   T
    1/2 SmaI site         A CCC GGG
                       SmaI site
            GGG CCC

FIG. 2A

DGLI (23-mer)  5'  GG  GCA  CAT  GGT  TTG  TTT  GGA  AAA  3'
                               C    C    T
                                         A LPC2 (17-mer)  5'  ACT  ACT  ATC  ACG  TAG  TA  3'

FIG. 2B

P = Pst I
H = Hind III
E = EcoR I
B = BamH I

S1 = Universal primer site
S2 = Universal reverse primer site

```
           C
           L
           A
           1
        GAATTCAGTATTGACAATTTATACATCGATATGGTATAAATGTGTGGAATTGTGAGCGGAT
        ----+----+----+----+----+----+----+----+----+----+----+----+  60
E       CTTAAGTCATAACTGTTAAATATGTAGCTATACCATATTACACACCTTAACACTCGCCTA
C
R            B           H        P   B        X  S
1            G           I        V   A        B  A
             L           N        U   M        A  L
             2           3        2   1        1  1

AACAATTTCACACAGGAGATCTGCAGGTAAGCTTCAGCTGGGATCCTCTAGAGTCGACGT
        ----+----+----+----+----+----+----+----+----+----+----+----+ 120
        TTGTTAAAGTGTGTCCTCTAGACGTCCATTCGAAGTCGACCCTAGGAGATCTCAGCTGCA
                                                   N
                                                   D
                                                   E
                                                   1

GAAAAATGGGCGCACATTGTGCGACATTTTTTTGTCATATG
        ----+----+----+----+----+----+----+----+ 161
        CTTTTTACCGCGTGTAACACGCTGTAAAAAAACAGTATAC
```

FIG. 6

```
        v10        v20        v30        v40        v50        v60        v70
         +----------+----------+----------+----------+----------+----------+
TTGTTTGGAA AATTACATCC CACAAACCCT GAAGTGACCA TGAATATAAG TCAGATGATC ACCTACTGGG
         +----------+----------+----------+----------+----------+----------+
        v80        v90       v100       v110       v120       v130       v140

GATACCCAGC TGAGAATATT GAAGTTGTGA CCGAAGACGG TTATATCCTT GGGATGACA GAATTCCTTA
         +----------+----------+----------+----------+----------+----------+
       v150        v160       v170       v180       v190       v200       v210

TGGGAGGAAA AATTCAGAGA ATATAGGCCG GAGACCTGTT GCATTTTTGC AACACGGTTT GCTCGCATCA
         +----------+----------+----------+----------+----------+----------+
       v220        v230       v240       v250       v260       v270       v280

GCCACAAACT GGATCTCCAA CCTGCCCAAC AACAGCCTGG CCTTCATCCT GGCCGACGCC GGGTACGACG
         +----------+----------+----------+----------+----------+----------+
       v290        v300       v310       v320       v330       v340       v350

TGTGGCTGGG GAACAGCAGG GGCAACACCT GGGCCAGGAG GAATCTGTAC TACTGCCCG ACTCCGTCGA
         +----------+----------+----------+----------+----------+----------+
       v360        v370       v380       v390       v400       v410       v420

ATTCTGGGCT TTCAGCTTTG ACGAGATGGC TAAATATGAC CTTCCCGCCA CCATTGACTT CATCTTGAAG
         +----------+----------+----------+----------+----------+----------+
       v430        v440       v450       v460       v470       v480       v490

AAAACGGGAC AGGACAAGCT ACACTAGTT GGCCATTCCC AGGCACCAC CATTGGTTTC ATCGCCTTTT
         +----------+----------+----------+----------+----------+----------+
       v500        v510       v520       v530       v540       v550       v560

CCACCAATCC CAAGCTGGCG AAACGGATCA AAACCTTCTA TGCATTAGCT CCCGTTGCCA CCGTGAAGTA
```

FIG. 8A

```
                                                      v570        v580        v590        v600        v610        v620        v630
                                                        +-----------+-----------+-----------+-----------+-----------+-----------+
                                              CACCGAAACC CTGTTAAACA AACTCATGCT CGTCCCCTTG TTCCTCTTCA AGCTTATATT TGGAAACAAA
                                              -----------+-----------+-----------+-----------+-----------+-----------+-----------
                                                      v640        v650        v660        v670        v680        v690        v700

ATATTCTACC CACACCACTT CTTTGATCAA TTTCTCGCCA CCGAGGTATG CTCCCGGCAG ACGGTGGATC
                                              -----------+-----------+-----------+-----------+-----------+-----------+-----------
                                                      v710        v720        v730        v740        v750        v760        v770

TCCTCTGCAG CAACGCCCTG TTTATCATTT GTGGATTTGA CACTATGAAC TTGAACATGA GTCGCTTGA
                                              -----------+-----------+-----------+-----------+-----------+-----------+-----------
                                                      v780        v790        v800        v810        v820        v830        v840

TGTGTATCTG TCACATAATC CAGCAGGAAC ATCGGTTCAG AAGGTGCTCC ACTGGTCCCA GGCTGTTAAG
                                              -----------+-----------+-----------+-----------+-----------+-----------+-----------
                                                      v850        v860        v870        v880        v890        v900        v910

TCTGGGAAGT TCCAAGCTTT TGACTGGGGA AGCCCAGTTC AGAACATGAT GCACTATCAT CAGAGCATGC
                                              -----------+-----------+-----------+-----------+-----------+-----------+-----------
                                                      v920        v930        v940        v950        v960        v970        v980

CTCCCTACTA CAACCTGACA GACATGCATG TGCCAATCGC AGTGTGGAAC GGTGGCAACG ACTTGCTGGC
                                              -----------+-----------+-----------+-----------+-----------+-----------+-----------
                                                      v990        v1000       v1010       v1020       v1030       v1040

CGACCCTCAC GATGTTGACC TTTTGCTTTC CAAGCTCCCC AATCTCATTT ACCACAGGAA GATTCCTCCT
                                              -----------+-----------+-----------+-----------+-----------+-----------+-----------
                                                      v1060       v1070       v1080       v1090       v1100       v1110

TACAATCACT TGGACTTTAT CTGGGCCATG GATGCCCCTC AAGCGGTTTA CAATGAAATT GTTTCCATGA
```

FIG. 8B

```
            v1130       v1140       v1150       v1160       v1170       v1180
      ----------+-----------+-----------+-----------+-----------+-----------+
TGGAACAGA TAATAAGTAG TTCTAGATTT AAGGAATTAT TCTTTTATTG TTCCAAAATA CGTTCTTCTC
      ----------+-----------+-----------+-----------+-----------+-----------+
            v1200       v1210       v1220       v1230       v1240       v1250

TCACACGTGG TTTTCTATCA TGTTTGAGAC ACGGTGATTG TTCCCATGGT TTTGATTTCA GAAATGTGTT
      ----------+-----------+-----------+-----------+-----------+-----------+
            v1270       v1280       v1290       v1300       v1310       v1320

AGCATCAACA ATCTTTCCAT TGGTAATTTT TGAATTTAAA ATGATTTTTA AATTTGGGGC ATCTGGGTGG
      ----------+-----------+-----------+-----------+-----------+-----------+
            v1340       v1350       v1360       v1370       v1380       v1390

CTCAGTTGGC TAAGTCGTCT GCCTTGGCTT AAGTCATGAT CTCGGGGTCC TAGGATGGAG CCTTGTGTCT
      ----------+-----------+-----------+-----------+-----------+-----------+
            v1410       v1420       v1430       v1440       v1450       v1460

GGGCTCCCTG CGGGGCGGGG GTCTGCTTCT CCTCCCCTG CTCCCCCCTG CTGCTGTGTG CACACACGCT
      ----------+-----------+-----------+-----------+-----------+-----------+
            v1480       v1490       v1500       v1510       v1520

CTCTCTCTCT CAAATAAATA AATAAATAAA TACTTAATAA AATAAAAAAA AAAAAAAA
      ----------+-----------+-----------+-----------+-----------+.
```

FIG. 8C

| | | | | | | | | | |
|---|---|---|---|---|---|---|---|---|---|
| | | | | – | | | | – | |
| 1 | Leu | Phe | Gly | Lys | Leu | His | Pro | Thr | Asn | Pro | 10 |
| 11 | Glu | Val | Thr | Met | Asn | Ileu | Ser | Gln | Met | Ile | 20 |
| 21 | Thr | Tyr | Trp | Gly | Tyr | Pro | Ala | Glu | Glu | Tyr | 30 |
| 31 | Glu | Val | Val | Thr | Glu | Asp | Gly | Tyr | Ile | Leu | 40 |
| 41 | Gly | Ile | Asp | Arg | Ile | Pro | Tyr | Gly | Arg | Lys | 50 |
| | | | | , | | | – | | + | |
| 51 | Asn | Ser | Glu | Asn | Ile | Gly | Arg | Arg | Pro | Val | 60 |
| 61 | Ala | Phe | Leu | Gln | His | Gly | Leu | Leu | Ala | Ser | 70 |
| 71 | Ala | Thr | Asn | Trp | Ile | Ser | Asn | Leu | Pro | Asn | 80 |
| 81 | Asn | Ser | Leu | Ala | Phe | Ile | Leu | Ala | Asp | Ala | 90 |
| 91 | Gly | Tyr | Asp | Val | Trp | Leu | Gly | Asn | Ser | Arg | 100 |
| | | | | , | | – | | | + | |
| 101 | Gly | Asn | Thr | Trp | Ala | Arg | Arg | Asn | Leu | Tyr | 110 |
| 111 | Tyr | Ser | Pro | Asp | Ser | Val | Glu | Phe | Trp | Ala | 120 |
| 121 | Phe | Ser | Phe | Asp | Glu | Met | Ala | Lys | Tyr | Asp | 130 |
| 131 | Leu | Pro | Ala | Thr | Ile | Asp | Phe | Ile | Leu | Lys | 140 |
| 141 | Lys | Thr | Gly | Gln | Asp | Lys | Ser | Leu | His | Tyr | Val | 150 |
| | | | | , | | | | – | + | |
| 151 | Gly | His | Ser | Gln | Gly | Thr | Thr | Ile | Gly | Phe | 160 |
| 161 | Ile | Ala | Phe | Ser | Thr | Asn | Pro | Lys | Leu | Ala | 170 |
| 171 | Lys | Arg | Ile | Lys | Thr | Phe | Tyr | Ala | Leu | Ala | 180 |

```
181  Pro Val Ala Thr Val Lys Tyr Thr Glu Thr  190
191  Leu Leu Asn Lys Leu Met Leu Val Pro Ser  200
                                       -   +
201  Phe Leu Phe Lys Leu Ile Phe Gly Asn Lys  210
211  Ile Phe Tyr Pro His His Phe Asp Asp Gln(?) 220
221  Phe Leu Ala Thr Glu Val Cys Ser Arg Glu  230
231  Thr Val Asp Leu Leu Cys Ser Asn Ala Leu  240
241  Phe Ile Cys Gly Phe Asp Thr Met Asn(?)    250
                                       -   +
251  Leu Asn Met Ser Arg Leu Asp Val Tyr Leu  260
261  Ser His Asn Pro Ala Gly Thr Ser Val Gln  270
271  Asn Val Leu His Trp Ser Gln Ala Val Lys  280
281  Ser Gly Lys Phe Gln Ala Phe Asp Trp Gly  290
291  Ser Pro Val Gln Asn Met Met His Tyr His  300
                                       -   +
301  Gln Ser Met Pro Pro Tyr Tyr Asn Leu Thr  310
311  Asp Met His Val Pro Ile Ala Val Trp Asn  320
321  Gly Gly Asn Asp Leu Leu Ala Asp Pro His  330
331  Asp Val Asp Leu Leu Ser Lys Lys Leu Pro  340
341  Asn Leu Ile Tyr His Arg Lys Ile Pro Pro  350
                                       -   +
351  Tyr Asn His Leu Asp Phe Ile Trp Ala Met  360
361  Asp Ala Pro Gln Ala Val Tyr Asn Glu Ile  370
371  Val Ser Met Met Gly Thr Asp Asn Lys      379
```

FIG. 9B1

84.7% identity

```
             10v       20v       30v       40v       50v       60v
DGLM  LFGKLHPTNPEVTMNLSQMITYWGYPAEEYEVVTEDGYILGIDRIPYGRKNSENIGRRPVA
HGL   LFGKLHP.:PEVTMN:SQMITYWGYP.EEYEVTEDGYIL.::RIPYG:KNS.N.G:RPV.
      LFGKLHPGSPEVTMNISQMITYWGYPNEEYEVVTEDGYILEVNRIPYGKKNSGNTGQRPVV
            ^30        ^50        ^70        ^80
             70v       80v       90v      100v      110v      120v
DGLM  FLQHGLLASATNWISNLPNNSLAFILADAGYDVWLGNSRGNTWARRNLYYSRPSVEFWAFS
HGL   FLQHGLLASATNWISNLPNNSLAFILADAGYDVWLGNSRGNTWARRNLYYS.SVEFWAFS
      FLQHGLLASATNWISNLPNNSLAFILADAGYDVWLGNSRGNTWARRNLYYSPDSVEFWAFS
            ^90       ^110       ^130       ^140
            130v      140v      150v      160v      170v      180v
DGLM  FDEMAKYDLPATIDFILKKTGQDKLHYVGHSQGTTIGFIAFSTNPKLAKRIKTFYALAPVA
HGL   FDEMAKYDLPATIDFI:KKTGQ.:LHYVGHSQGTTIGFIAFSTNP.LAKRIKTFYALAPVA
      FDEMAKYDLPATIDFIVKKTGQKQLHYVGHSQGTTIGFIAFSTNPSLAKRIKTFYALAPVA
           ^150       ^170                ^180
            190v      200v      210v      220v      230v      240v
DGLM  TVKYTETLLNKLMLVPSFLFKLIFGNKIFYPHHFFDQFLATEVCSRETVDLLCSNALFIIC
HGL   TVKYT.:L:NKL..:VP  LFK:IFG:KIFYPH:FFDQFLATEVCSRE::LLCSNALFIIC
      TVKYTKSLINKLRFVPQSLFKFIFGDKIFYPHNFFDQFLATEVCSREMLNLLCSNALFIIC
           ^210                ^230       ^250       ^260
```

```
              250v         260v         270v         280v         290v         300v
DGLM    GFDTMNLNMSRLDVYLSHNPAGTSVQNVLHWSQAVKSGKFQAFDWGSPVQNMMHYHQSMPP
HGL     GFD:.N:N SRLDVYLSHNPAGTSVQN::HW:QAVKSGKFQA:DWGSPVQN.MHY:QS PP
              270^         280^         290^         300^         310^         320^

310v         320v         330v         340v         350v         360v
DGLM    GFDSKNFNTSRLDVYLSHNPAGTSVQNMFHWTQAVKSGKFQAYDWGSPVQNRMHYDQSQPP
        YYNLTDMHVPIAVWNGGNDLLADPHDVDLLLSKLPNLIYHRKIPPYNHLDFIWAMDAPQAV
HGL     YYN:T.M:VPIAVWNGG:DLLADP:DV:LLL:KLPNLIYH:.IP YNHLDFIWAMDAPQ.V
              330^         340^         350^         360^         370^         380^
              370v
DGLM    YYNVTAMNVPIAVWNGGKDLLADPQDVGLLLPKLPNLIYHKEIPFYNHLDFIWAMDAPQEV

DGLM    YNEIVSMMGTDNK
HGL     YN:IVSM::.D:K
        YNDIVSMISEDKK
              390^
```

FIG. 9B2

75.7% identity

```
                 10v       20v       30v       40v       50v       60v
DGLM    LFGKLHPFTNPEVTMNLSQMITYWGYPAEEYEVVTEDGYILGIDRIPYGRKNSENIGRRPVA
        LFGKL P.NPE..MN:SQMITYWGYP :EYEVVTEDGYILG: RIP.G::NSENIG:RPV.
RATLL   LFGKLGPGNPEANMNISQMITYWGYPCQEYEVVTEDGYILGVYRIPHGKNNSENIGKRPVV
              40^       50^       60^       70^       80^       90^

70v       80v       90v      100v      110v      120v
DGLM    FLQHGLLASATNWISNLPNNSLAFILADAGYDVWLGNSRGNTWARRNLYYSRPSVEFWAFS
        :LQHGL: ASATNWI:NLPNNSLAF:LADAGYDVWLGNSRGNTW:R:N:YYS. SVEFWAFS
RATLL   YLQHGLIASATNWIANLPNNSLAFMLADAGYDVWLGNSRGNTWSRKNVYYSPDSVEFWAFS
              100^      110^      120^      130^      140^      150^

130v      140v      150v      160v      170v      180v
DGLM    FDEMAKYDLPATIDFILKKTGQDKLHYVGHSQGTTIGFIAFSTNPKLAKRIKTFYALAPVA
        FDEMAKYDLPATI:FI::KTGQ:K::HYVGHSQGTTIGFIAFSTNP.LAK:IKTFYALAPVA
RATLL   FDEMAKYDLPATINFIVQKTGQEKIHYVGHSQGTTIGFIAFSTNPTLAKKIKTFYALAPVA
              160^      170^      180^      190^      200^      210^

190v      200v      210v      220v      230v      240v
DGLM    TVKYTETLLNKLMLVPSFLFKLIFGNKIFYPHHFFDQFLATEVCSRETVDLLCSNALFIIC
        TVKYT:: L:K: ::P:FLFKL::P:FLFKL:FG:K:F PH :FD:FL:TEVCSRE.:DLLCSN:LFI:C
RATLL   TVKYTQSPLKKISFIPTFLFKLMFGKKMFLPHTYFDDFLGTEVCSREVLDLLCSNTLFIFC
              230^      240^      250^      260^      270^
```

FIG. 9C1

```
              250v        260v        270v         280v         290v          300v
DGLM     GFDTMNLNMSRLDVYLSHNPAGTSVQNVLHWSQAVKSGKFQAFDWGSPVQNMMHYHQSMPP
         GFD..NLN:SR:DVYL:HNPAGTSVQ: LHW:Q V:SGKFQAF:WGSP QNM:HY:Q. PP
RATLL    GFDKKNLNVSRFDVYLGHNPAGTSVQDFLHWAQLVRSGKFQAFNWGSPSQNMLHYNQKTPP
              290^        300^        310^         320^         330^
              310v        320v        330v         340v         350v          360v
DGLM     YYNLTDMHVPIAVWNGGNDLLADPHDVDLLLSKLPNLIYHRKIPPYNHLDFIWAMDAPQAV
         Y:::.M VP:AVWNGGND:LADP:DV..:LL:KL:NL::H:.I  : YNHLDFIWAMDAPQ.V
RATLL    EYDVSAMTVPVAVWNGGNDILADPQDVAMLLPKLSNLLFHKEILAYNHLDFIWAMDAPQEV
              350^        360^        370^         380^         390^         400^
              370v
DGLM     YNEIVSMMGTDNK
         YNE::SMM:.D.K
RATLL    YNEMISMMAED
              410^
```

FIG. 9C2

81.0% identity

```
         10v          20v          30v          40v          50v          60v
DGLM LFGKLHPTNPEVTMNLSQMITYWGYPAEEYEVVTEDGYILGIDRIPYGRKNSENIGRRPVA
     LFGK  PTNPEV.MN:SQMI:YWGYP:E.YEVVTEDGYIL.::RIPYG:KNS.N G:RPV.
RGLM LFGKSAPTNPEVNMNISQMISYWGYPSEKYEVVTEDGYILEVNRIPYGKKNSGNRGQRPVV
         10^          20^          30^          40^          50^          60^
         70v          80v          90v         100v         110v         120v
DGLM FLQHGLLASATNWISNLPNNSLAFILADAGYDVWLGNSRGNTWARRNLYYSRPSVEFWAFS
     FLQHGLLASA:NWISNLPNNSLAFILADAGY:VWLGNSRGNTW:RRNLYYS. SVEFWAFS
RGLM FLQHGLLASASNWISNLPNNSLAFILADAGYGVWLGNSRGNTWSRRNLYYSPDSVEFWAFS
         70^          80^          90^         100^         110^         120^
        130v         140v         150v         160v         170v         180v
DGLM FDEMAKYDLPATIDFILKKTGQDKLHYVGHSQGTTIGFIAFSTNPKLAKRIKTFYALAPVA
     FDEMAKYDLPATIDFI::K.TGQ:KLHYVGHSQGTTIGFIAFSTNPKLA.RIKTFYALAPVA
RGLM FDEMAKYDLPATIDFIVKETGQEKLHYVGHSQGTTIGFIAFSTNPKLAERIKTFYALAPVA
        130^         140^         150^         160^         170^         180^
        190v         200v         210v         220v         230v         240v
DGLM TVKYTETLLNKLMLVPSFLFKLIFGNKIFYPHHFFDQFLATEVCSRETVDLLCSNALFIIC
     TVKYT.:L:NKL.::P: :FK:IFG:KIFYPH:FFDQFLAT:VCSRET::::CSNALFIIC
RGLM TVKYTKSLVNKLRFIPPTMFKIIFGDKIFYPHNFFDQFLATQVCSRETLNVICSNALFIIC
        190^         200^         210^         220^         230^         240^
```

FIG. 9D1

```
              250v       260v       270v       280v       290v       300v
DGLM    GFDTMNLNMSRLDVYLSHNPAGTSVQNVLHWSQAVKSGKFQAFDWGSPVQNMMHYHQSMPP
        GFD: NLNMSRLDVY:SHNPAGTSVQN:LHW:QAVKSG:FQAF:WGSP.QN::H::Q: PP
RGLM    GFDSANLNMSRLDVYVSHNPAGTSVQNMLHWTQAVKSGNFQAFNWGSPAQNVVHFNQPTPP
              250^       260^       270^       280^       290^       300^

310v       320v       330v       340v       350v       360v
DGLM    YYNLTDMHVPIAVWNGGNDLLADPHDVDLLLSKLPNLIYHRKIPPYNHLDFIWAMDAPQAV
        YYN:T.M:VPIAVW:GGND LADP:DVDLLL:KL:NLIYH:.I PYNHLDFIWAM:APQ.V
RGLM    YYNVTAMNVPIAVWSGGNDWLADPQDVDLLLPKLSNLIYHKEILPYNHLDFIWAMNAPQEV
              310^       320^       330^       340^       350^       360^

370v
DGLM    YNEIVSMMGTDNK
        YNEI:SMM:.D:K
RGLM    YNEIISMMAKDKK
              370^

FIG. 9D2
```

1 = RGL
2 = pRGLNC1.3I
3 = pRGLNC1.3NI
4 = pRUI
5 = pRUNI
6 = pDGL5.303I
7 = pDGL5.303NI
8 = DGL

POLYPEPTIDE DERIVATIVES OF DOG GASTRIC LIPASE AND PHARMACEUTICAL COMPOSITIONS CONTAINING SAME

CROSS-REFERENCE TO RELATED APPLICATIONS

This application is a division of U.S. application Ser. No. 08/227,108, filed Apr. 13, 1994, which is a national application filed from PCT/FR93/01260, filed Dec. 16, 1993, which is related to French patent application 92.15201, files Dec. 16, 1992.

BACKGROUND OF THE INVENTION

The present invention relates to nucleic acids encoding dog gastric lipase (DGL), and other polypeptide derivatives of the latter possessing a lipase activity, as well as their use, especially for the production of these polypeptides. The subject of the invention is also the polypeptides encoded by these nucleic acids, and the use of these polypeptides in pharmaceutical compositions.

DGL is a glycoprotein of about 380 amino acids (AA) of a molecular weight of about 49 kilodaltons (KD) synthesized in the form of a precursor containing a signal peptide at the amino-terminal ($NH_2$-terminal) end and secreted by the median cells of dog stomach fundic mucosa (Carriére F. et al. Eur. J. Biochem. 202 (1991) 75–83).

This enzyme belongs to a family of so-called "preduodenal" lipases of which certain members have already been purified and sometimes even cloned (Docherty A. J. P. et al., Nucl. Ac. res. 13 (1985) 1891–1903; Bodmer M. W. et al., Biochem. Biophys. Act. 909 (1987) 237–244; Moreau H. et al., Biochem. Biophys. Act. 960 (1988) 286–293; European Patents No. 0,191,061 and No. 0,261,016).

For a long time, it was taken for granted that the hydrolysis of food lipids occurred in the small intestine by virtue of the action of enzymes produced by the pancreas (Bernard C., C.R. Acad. Sci. 28 (1849) 249–253).

Observations suggested, however, that the hydrolysis of triglycerides could occur in the stomach by means of preduodenal enzymes (Volhard, F., Z. Klin. Med. 42 (1901) 414–429; Shonheyder, F. and Volquartz, K. Acta Physiol. Scand. 9 (1945) 57–67). These enzymes, and in particular dog gastric lipase, have enzymatic and physico-chemical properties which distinguish them from mammalian pancreatic lipases. These differences between gastric and pancreatic lipases essentially relate to the following points: molecular weight, amino acid composition, resistance to pepsin, substrate specificity, optimum pH for action, and stability in acidic medium.

Furthermore, in vitro, under certain conditions, a synergy of action between gastric and pancreatic lipases can be detected on the hydrolysis of long-chain triglycerides (Gargouri, Y. et al., Biochem. Biophys. Act. 1006 (1989) 255–271).

Several pathological conditions (cystic fibrosis, pancreatic exocrine insufficiency) are known where the patients totally or partially lack pancreatic exocrine secretion and therefore the enzymes necessary for the hydrolysis of foods (amylases, lipases, proteases). The non-absorption of fats at the intestinal level, and especially long-chain triglycerides, results in a very substantial increase in steatorrhea in these patients and in a very substantial slowing down of weight gain in young patients. In order to overcome this, pig pancreatic extracts are administered to these subjects at the time of meals. The therapeutic efficacy of these extracts could be greatly improved by the co-prescription of DGL by virtue of its specificity of action on long-chain triglycerides.

The purification and the determination of the NH2-terminal sequence of DGL are described in the article by F. Carriére which appeared in Eur. J. Biochem. 201, 75–83, 1991. A process permitting the extraction of this enzyme from dog stomachs is also described in this publication. This process consists essentially in subjecting dog stomachs to an extraction by an acidic aqueous medium (pH 2.5); the-lipase extract is precipitated by addition of water-soluble salts, then by a filtration on a molecular sieve, followed by a separation by ion-exchange chromatographies, as well as by gel filtration, and an elution fraction containing the lipase is recovered. The purified DGL obtained by these processes has a molecular weight according to the Laemmli technique of 49,000 daltons, of which 6000 correspond to sugars and 43,000 to a protein.

Obvious reasons of difficulties of supply of dog stomachs prevent any development of this process both at the laboratory level and at the industrial level, hence the necessity to find a process avoiding the use of dog stomachs, which makes it possible to produce DGL in a large quantity.

SUMMARY OF THE INVENTION

The aim of the present invention is precisely to permit the production of DGL on an industrial scale by removing any problem of supply of raw material, and at an advantageous cost price.

The invention stems from the discovery made by the inventors of the nucleotide sequence of the messenger RNA (mRNA) encoding DGL, after cloning of the complementary DNA (cDNA) of this mRNA by means of a probe corresponding to the nucleotide sequence of the rabbit recombinant gastric lipase described in the French patent application filed on Nov. 13, 1991 and published under the number 2 683 549.

The present invention relates to a nucleic acid that is constituted by a first DNA fragment represented in FIG. 8 (SEQ ID NO 1), or a second DNA fragment delimited by the nucleotides situated at positions 1 and 1137 (SEQ ID NO 2) of the DNA represented in FIG. 8, wherein either of the first or second DNA fragments encodes the polypeptide delimited by the amino acids situated at positions 1 and 379 (SEQ ID NO 3) of the amino acid sequence represented in FIG. 9A, this polypeptide corresponding to dog gastric lipase.

The invention also relates to a recombinant nucleic acid comprising one of the nucleic acids described above which is inserted into a nucleotide sequence which is heterologous with respect to such nucleic acids. This recombinant nucleic acid comprises a promoter situated upstream of the nucleic acid under whose control the nucleic acid is transcribed, as well as a sequence encoding signals for termination of transcription which is situated downstream of the nucleic acid.

Other embodiments of the invention relate to a recombinant vector, a host cell and a process for preparing a polypeptide. The vector comprises one of these recombinant nucleic acids and elements necessary for promoting and controlling the expression of these nucleic acids in a host cell, and more particularly to a promoter recognized by the polymerases of the host cell. The host cell, particularly of the prokaryotic or eukaryotic type, is transformed by the recombinant vector. This host cell comprises one of the recombinant nucleic acids defined herein and the regulatory elements which permit the expression of these nucleic acids. Also disclosed is a process for the preparation of a polypeptide encoded by a nucleic acid, comprising the steps of culturing one of these host cells in an appropriate culture medium, and recovering the polypeptide produced by the host cell, either directly from the culture medium, or after lysis of the host cell.

BRIEF DESCRIPTION OF THE DRAWINGS

The present invention will be more particularly illustrated by means of FIGS. 1 to 12, whose legends are the following:

FIG. 1: Polypeptide sequences of the cleavage region of rabbit (SEQ ID NO:12), human (SEQ ID NO:13) and rat (SEQ ID NO:14) gastric lipase precursors, and comparison with the NH$_2$-terminal sequence of dog gastric lipase (SEQ ID NO 11).

FIG. 2A: Design of a degenerate oligonucleotide (DGL,) encoding the cleavage region of the DGL precursor from comparison of its rabbit (SEQ ID NO:20), human (SEQ ID NO:19) and rat (SEQ ID NO:21) homologs.

FIG. 2B: Sequence of the oligonucleotides DGL, (SEQ ID NO 7) and DPL2 (SEQ ID NO 8).

FIG. 6: Nucleotide sequence (SEQ ID NO:15) of the EcoRI-Ndel DNA fragment of the plasmid pRU303.

FIG. 8: Nucleotide sequence of the CDXA encoding the mature DGL (SEQ ID NO 1). This FIG. 8 includes drawings 8A, 8B and 8C.

FIG. 9A: Polypeptide sequence of the mature DGL (SEQ ID NO 3). This FIG. 9A includes drawings 9A1 and 9A2.

FIG. 9B: Comparison of the polypeptide sequences of HGL (human gastric lipase) (SEQ ID NO:16) and DGL, and determination of the % homology. This FIG. 9B includes drawings 9B1 and 9B2.

FIG. 9C: Comparison of the polypeptide sequences of RATLL (rat lingual lipase) (SEQ ID NO:17) and DGL, and determination of the % homology. This FIG. 9C includes drawings 9C1 and 9C2.

FIG. 9D: Comparison of the polypeptide sequences of RGL (rabbit gastric lipase) (SEQ ID NO:18) and DGL, and determination of the % homology. This FIG. 9D includes drawings 9D1 and 9D2.

DETAILED DESCRIPTION OF THE INVENTION

Figure 3:
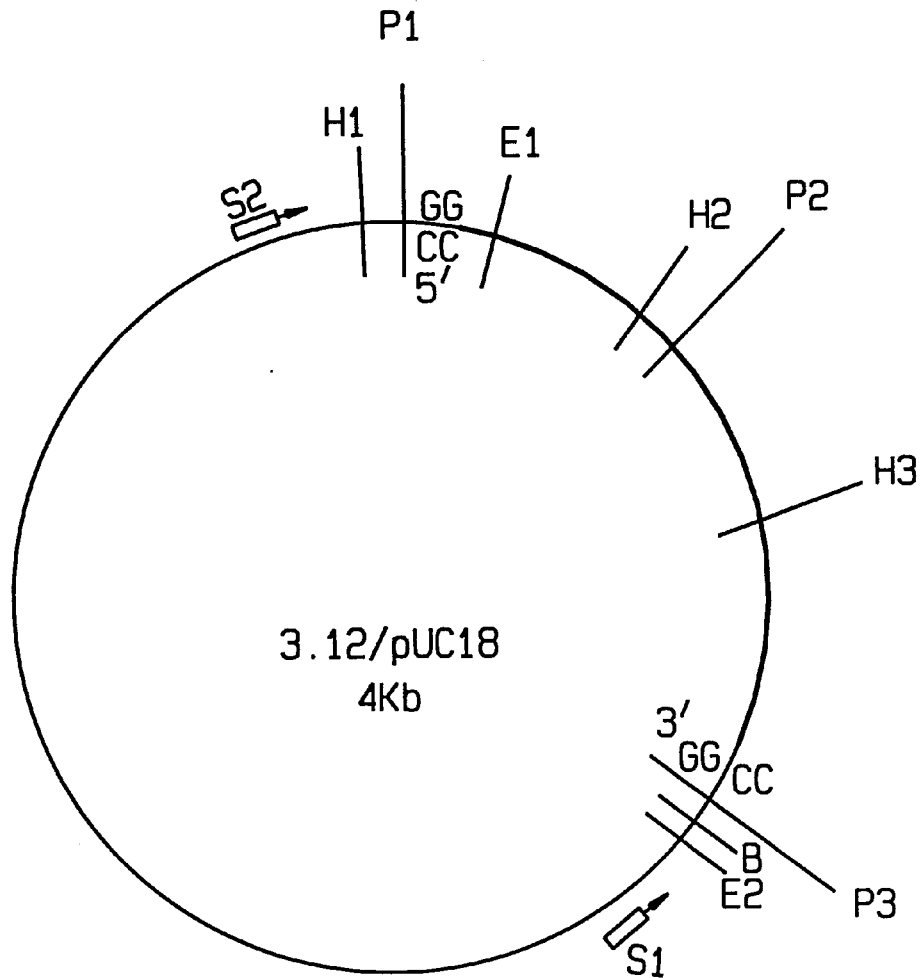
FIG. 3: Map of the-clone 3.12.

The present invention relates to any nucleic acid characterized in that it comprises all or part of the DNA fragment represented in FIG. 8 (SEQ ID NO 1), and more particularly all or part of the DNA fragment delimited by the nucleotides situated at positions 1 and 1137 (SEQ ID NO 2) of the DNA represented in FIG. 8, this DNA fragment encoding the polypeptide delimited by the amino acids situated at positions 1 and 379 of the amino acid sequence represented in FIG. 9A (SEQ ID NO 3), this polypeptide corresponding to the mature DGL.

The expression DGL, above and below, is understood to mean any lipase secreted by the gastric mucous membrane or by a pregastric raucous membrane in dogs.

The above mentioned nucleic acids may also comprise, upstream of the DNA fragment delimited by the nucleotides situated at positions 1 and 1137, of FIG. 8, a DNA fragment (more particularly a sequence ATG) encoding a methionine (SEQ ID NO 4).

The invention also relates to the above mentioned DNA fragments having, upstream of position 1137, a STOP codon, especially that consisting of the sequence delimited by the nucleotides situated at positions 1138, 1139 and 1140 of FIG. 8 (SEQ ID NO 6).

DGL, like all gastric lipases purified or cloned up until now, is synthesized in the form of a precursor consisting of a signal peptide preceding the polypeptide sequence of the mature protein.

Generally, the invention relates to any nucleic acid characterized in that it comprises, upstream of one of the above mentioned DNA fragments, a nucleotide sequence encoding a signal peptide.

As opposed to the double-stranded nucleic acids mentioned above, the invention also relates to the single-stranded nucleic acids consisting of either of the two complementary nucleotide sequences constituting the above mentioned DNA fragments.

The invention also relates to any nucleic acid capable of hybridizing with a single-stranded nucleic acid as described above, especially under the hybridization conditions mentioned in the following detailed description of the cloning of the CDNA of the DGL according to the invention.

Any nucleic acid encoding a polypeptide according to the invention and whose nucleotide sequence differs, according to the degeneracy of the genetic code, from the above mentioned nucleotide sequences, also enters within the scope of the present invention.

The subject of the invention is also any recombinant nucleic acid characterized in that it comprises a nucleic acid as described above according to the invention, inserted into a DNA molecule which is heterologous with respect to the above mentioned nucleic acid.

In this respect, the subject of the invention is more particularly any recombinant nucleic acid comprising a promoter situated upstream of the nucleic acid according to the invention, and under the control of which the transcription of the said nucleic acid is capable of being carried out, as well as a sequence encoding signals for termination of transcription which is situated downstream of the said nucleic acid.

The invention also relates to any recombinant vector, especially of the plasmid, cosmid or phage type, characterized in that it contains a recombinant nucleic acid as described above, inserted at one of its sites which are non-essential for its replication.

The recombinant vectors according to the invention are advantageously characterized in that they contain, at one of their sites which are non-essential for their replication, elements necessary for promoting and controlling the expression of a nucleic acid according to the invention in a host cell, and more particularly a promoter recognized by the polymerases of the cellular host, especially an inducible promoter.

The invention also relates to any cellular host, of the prokaryotic or eukaryotic type, transformed by a recombinant vector as described above, and comprising the regulatory elements permitting the expression of a gene or a cDNA according to the invention.

By way of examples of host cells capable of being transformed by a recombinant vector according to the invention, there may be mentioned mammalian cells such as COS or CHO cells, cells of insects capable of being infected by a recombinant virus of the baculovirus type, filamentous fungi such as Aspergillus niger or oryzae, yeasts such as *Saccharomyces cerevisiae* or *Kluyveromyces lactis*, as well as bacteria such as *E. coli* (Gram-negative bacterium) or *B. subtilis* (Gram-positive bacterium).

The subject of the invention is also DNA (or RHA) primers which can be used for the synthesis of nucleic acids according to the invention by the DNA chain amplification technique, designated below by PCR (Polymerase Chain Reaction) technique. This technique is more particularly described in U.S. Pat. Nos. 4,683,202 and 4,683,195, as well as in European Patent No. 200,362. The primers according to the invention advantageously consist of about 15 to 40 nucleotides corresponding to the 31 and 51 ends of either of the two strands constituting the above mentioned DNA fragments.

The invention also relates to nucleotide probes derived from either of the two strands constituting the above mentioned DNA fragments of the invention, as well as the use of these probes, especially for the detection in a biological sample of the possible presence of DGL.

Advantageously, the probes of the invention consist of about 17 to 23 nucleotides. The detection of the presence of DGL in a sample is preferably performed after amplification of the number of copies of the DGL-encoding genes or mRNAs which may be present in this sample, by means of the primers indicated above.

In this respect, the invention also relates to a kit for implementing the above mentioned method of detection, comprising:

where appropriate, primers as described above, as well as the reagents for the preparation of a medium suitable for carrying out the amplification of the DNA or RNA sequence encoding DGL, a nucleotide probe as described above, labeled where appropriate, especially radioactively or enzymatically, as well as the reagents for the preparation of a medium suitable for carrying out the hybridization between the probe and the above mentioned DNA or RNA sequence, the reagents permitting the detection of the probe hybridized with the said sequence.

Advantageously, the nucleotide probes of the invention are capable of hybridizing both with the DNA or RNA sequence encoding DGL and with those encoding human gastric lipase (HGL) and rabbit gastric lipase (RGL). Such probes can be used for the implementation of a method of detection in vitro of the possible presence of HGL in a biological sample capable of containing the latter. Such a method of detection is carried out in the manner indicated above, and permits the in vitro diagnosis of pathologies linked to the overproduction, or conversely, to the insufficiency, or even the absence, of production of gastric lipase in the body.

The subject of the invention is also the polypeptides corresponding, according to the universal genetic -code, to the nucleic acids according to the invention described above, or any fragment of these recombinant polypeptides, or any polypeptide modified by substitution and/or addition and/or suppression of one or more amino acids of these recombinant polypeptides, these modified fragments or polypeptides preserving the enzymatic properties of the above mentioned recombinant polypeptides.

"Recombinant polypeptide" should be understood to mean any molecule possessing a polypeptide chain capable of being produced by genetic engineering, by transcription and translation of a corresponding DNA sequence under the control of appropriate regulatory elements inside an effective host cell. Consequently, the expression "recombinant polypeptides" does not exclude the possibility that these polypeptides have undergone pos-translational [sic] modifications such as glycosylation.

The term "recombinant" implies the fact that the polypeptide has been produced by genetic engineering, more particularly because of the fact that this polypeptide results from the expression in a host cell of nucleic acid sequences which have been previously introduced into an expression vector used in the said host.

However, it should be understood that this expression does not exclude the possibility that the polypeptide is produced by a different process, for example by conventional chemical synthesis according to the conventional methods used for the synthesis of proteins, or by cleavage of larger-sized molecules.

The invention also relates to the above mentioned polypeptides in biologically pure form. The expression "biologically pure" should be understood to mean, on the one hand, a degree of purity enabling the recombinant polypeptide to be used for the production of pharmaceutical compositions and, on the other hand, the absence of contaminants, more particularly of natural contaminants.

In this respect, the invention more particularly relates to:

the polypeptide delimited by the amino acids situated at position 1 and 379 of the amino acid sequence represented in FIG. 9A (SEQ ID NO 3), and corresponding to the mature DGL as obtained by genetic engineering, and whose molecular weight varies from about 43,200 to about 50,000 daltons, according to whether the host in which it is produced carries out post-translational modifications on the polypeptide chain of this DGL, the above mentioned polypeptides whose amino acid sequences are Preceded by a methionine (SEQ ID NO 5).

Advantageously, the above mentioned polypeptides according to the invention, and more particularly the recombinant DGL, possess a lipolytic activity of between about 50 U/mg of polypeptide and about 750 U/mg of polypeptide, and preferably greater than 250 U/mg of polypeptide when measured by means of a short-chain triglyceride (such as tributyrin), as substrate according to the Gargouri method (more particularly described in the detailed description which follows from the invention). One unit U corresponds to the quantity of enzyme necessary to liberate one $\mu$mol of $H^+$ ions (that is to say of free fatty acids) per minute at 37° C.

The maximum lipolytic activity of the recombinant polypeptides, according to the invention, on long-chain fatty acids is advantageously obtained at pH values of 3 to 5.

According to another advantageous aspect of the recombinant polypeptides of the invention, their lipolytic activity remains unchanged after incubation lasting for one hour at pH 2 and at 37° C.

The present invention also relates to a process for the preparation of a polypeptide as described above, this process comprising the following sequence of steps:

the culture of a host cell, transformed by a recombinant vector as described above, in an appropriate culture medium, and the recovery of the polypeptide produced by the said host cell, either directly from the above mentioned culture medium, when the sequence encoding the aid polypeptide is preceded by a signal sequence and the host cell is capable of secreting the polypeptide into the culture medium (especially in the case of eukaryotic cells and yeasts), or after lysis of the host cell (especially in the case of bacteria).

Where appropriate, the recovery step is followed by a step of purification of the recovered polypeptide, and especially after recovery by lysis of the bacterium by a step for solubilization of the polypeptide, then its renaturation.

The agents and techniques for solubilization of polypeptides obtained in the form of inclusions are well known to persons skilled in the art. Essentially, the solubilizing agents are urea, quaternary ammonium halides such as guanidinium chloride or cetyltrimethylammonium chloride which are used in experimental procedures such as those described by N. K. Purl et al. in Biochem. J (1992) 2850, 871–879.

Advantageously, as already specified above, the nucleotide sequences encoding the polypeptides whose production is desired, and inserted into the vector used to transform the host cells, are preceded by a signal sequence thus permitting the secretion of the polypeptides produced outside the host cells and their recovery directly from the culture medium without having to carry out the lysis of the said host cells.

By way of example, it will be possible to obtain the synthesis of the mature DGL in mammalian cells such as COS cells or CHO cells by inserting the nucleic acid encoding the DGL precursor into an appropriate expression vector.

The presence of the DNA segment encoding the signal peptide will pe=it the cellular machinery to glycosylate in the endoplasmic reticulum and to secrete the DGL in the culture medium in biologically active f o=.

Alternatively, it will be possible to obtain the production- of dog gastric lipase by insect cells by inserting the CDNA encoding DGL or its precursor behind an appropriate promoter in the genome o.f a virus of the baculovirus type which is capable of infecting the said cells.

In order to cause DGL to be produced and secreted by a yeast such as *Saccharomyces cerevisiae* or *Kluyveromyces lactis*, it will be preferable to replace, in the CDNA, the DNA segment encoding the signal peptide of the DGL by a DNA fragment encoding a signal peptide of yeast protein. The recombinant CDNA thus obtained will then be introduced into an expression vector specific for the host considered. Such expression systems are now relatively common. For example, there may be mentioned the expression of human serum albumin (European Patent No. 0,361,991 A2) or calf chymosin (Van den Berg J. A. et al., Biotechnology 8 (1990) 135–139).

*Escherichia coli* is a Gram-negative bacterium having a wall, in which the phenomena of secretion of proteins into the culture medium are extremely reduced. A certain number of proteins accumulate in the bacterial periplasm by virtue of the presence of signals similar to the signal sequences of eukaryotic proteins. Among the latter, there may be mentioned the products of the phoA and male genes for example. Certain regions of these genes have been used to produce heterologous proteins in the piroplasmic space of *E. coli*. However, the synthesis in the cytoplasm of foreign proteins remains the best-known system and the most frequently used in *E. coli*.

The observance of certain rules deduced from experience during the production of plasmid constructs makes it possible to optimize the level of expression of the proteins of interest.

In a first stage, it will be appropriate to place the cDNA encoding the mature part of DGL, that is to say lacking the segment encoding the signal peptide, behind a powerful bacterial or phage promoter. To avoid problems of possible toxicity of the foreign protein in the bacterium, a promoter will be preferably chosen which is inducible by a chemical agent (Lac or Trp promoters) or by a physical agent such as change of temperature (PL promoter and cI857 repressor). The CDNA should be contiguous, in its 51 terminal region, to an ATG sequence specifying the initiation of protein synthesis on the messenger RNA. This initiator ATG should be preceded, at a distance of 6 to 12 base pairs, by, a region rich in purines, called Shine-Dalgarno region, and corresponding, on the messenger RNA, to the ribosome-binding site.

It will be possible to modify the composition of the sequence of the DNA segment situated between the Shine-Dalgarno region and the initiator ATG so as to reduce the elements of secondary structure around the AUG initiation codon on the messenger RNA. Once the necessary modifications have been made, the vector will be introduced into an appropriate host.

The invention relates to the antibodies directed against the polypeptides of the invention, and more particularly those directed against DGL and capable of also recognizing HGL and RGL. Such antibodies can be obtained by immunization of an animal with these polypeptides followed by the recovery of the antibodies formed.

It goes without saying that this production is not limited to polyclonal antibodies.

It also applies to any monoclonal antibody produced by any hybridoma capable of. being formed, by conventional methods, from the spleen cells of an animal, especially mouse or rat, which are immunized against one of the purified polypeptides of the invention, on the one hand, and the cells of an appropriate myeloma on the other hand, and being selected for its capacity to produce monoclonal antibodies recognizing the polypeptide initially used for the immunization of the animals, as well as HGL.

The invention also relates to the use of these antibodies for the implementation of a method of detection or assay of DGL or of HGL in a biological sample capable of containing it.

The invention more particularly relates to the use of these antibodies for the implementation of a method of diagnosis in vitro of pathologies linked to the overproduction, or conversely, to the insufficiency, or even the absence of production of lipase in the body.

This in vitro diagnostic method, performed using a biological sample collected from a patient, comprises a step of bringing into contact with this sample, followed by a step of detection of the possible antibody-HGL complexes formed during the preceding step.

In this respect, the invention also relates to a kit for implementing a method of detection or diagnosis in vitro mentioned above, comprising:

antibodies as described above, advantageously labeled radioactively or enzymatically, as well as the reagents for the preparation of a medium suitable for carrying out the immunological reaction between these antibodies and HGL, the reagents permitting the detection of the immunological complexes formed between these antibodies and HGL.

The invention also relates to the use of one or more polypeptides described above, for the production of pharmaceutical compositions which can be used especially orally, intended to facilitate the absorption of the animal or vegetable fats ingested by a healthy individual or an individual suffering from one or more pathologies affecting or otherwise the level of production of gastric lipase. In particular, such compositions are advantageously used in individuals undergoing a medical treatment altering the mechanism of absorption of fats, or alternatively in elderly persons.

The invention relates more particularly to the use of one or more polypeptides described above for the production of medicinal products intended for the treatment of pathologies linked to the insufficiency, or even the absence, of production of lipases in the body, and more particularly of pathologies such as cystic fibrosis, and pancreatic exocrine insufficiency.

The subject of the invention is also pharmaceutical compositions comprising at least one polypeptide according to the invention, where appropriate in combination with one or several other polypeptides with lipase activity, in combination with a pharmaceutically acceptable vehicle.

The pharmaceutical compositions according to the invention are preferably administrable orally, and are provided especially in the form of hard gelatin capsules, tablets or powders for dilution.

The daily dosage in man is advantageously of about 400 mg to about 1,200 mg, preferably divided during the main meals, equivalent to an amount of about 130 mg to about 400 mg per meal.

The invention also relates to the use of the polypeptides as described above according to the invention or any other mammalian gastric lipase and derivatives of the said polypeptides, for the implementation of enzymatic bioconversion reactions (such as enzymatic hydrolyses or transesterifications), especially in immobilized form on a solid support.

In the case of the preparation of the nucleic acids of the invention, the latter can be carried out chemically, especially according to one of the following processes.

An appropriate mode of preparation of the nucleic acids (comprising a maximum of 200 nucleotides) of the invention by the chemical route comprises the following steps:

the synthesis of DNA using the automated β-cyanethyl phosphoramidite method described in Bioorganic Chemistry 4; 274–325, 1986, the cloning of the DNAs thus obtained into an appropriate plasmid vector and the recovery of the DNAs by hybridization with an appropriate probe.

A mode of preparation, by the chemical route, of nucleic acids of length greater than 200 nucleotides, comprises the following steps:

the assembly of chemically synthesized oligonucleotides, provided at their ends with various restriction sites, whose sequences are compatible with the amino acid linkage of the natural polypeptide according to the principle described in Proc. Nat. Acad. Sci. USA 80; 7461–7465, 1983, the cloning of the DNAs thus obtained into an appropriate plasmid vector and the recovery of the desired nucleic acid by hybridization with an appropriate probe.

The invention will be more particularly illustrated with the aid of the following detailed description of the construction of recombinant vectors according to the invention and their use for the production of DGL.

An RNA preparation was prepared from mucosa isolated from the fundic region of dog stomach. The messenger RNAs isolated by affinity chromatography on an oligo-dT cellulose column were converted into complementary DNA (CDNA) by the use of specific enzymes: Rous Sarcoma Virus reverse transcriptase and E. coli DNA polymerase I (Klenow fragment). This CDNA was introduced into the vector pUC18 after certain modifications and the recombinant molecules were used to transform the bacterium E. coli MM294. The transformant clones were screened by in situ hybridization by means of a probe containing the CDNA of radioactively labeled rabbit gastric lipase. After autoradiography, the bacterial colonies corresponding to a positive signal during the hybridization experiment were isolated and the plasmid DNA present in their cytoplasm amplified and purified.

After screening of the clones obtained, the clone 3.12 was selected and sequenced. This clone contains a PstI—PstI insert of 1201 base pairs, which insert is itself divided into two unequal parts H and L by a PstI restriction site.

No clone containing the complete CDNA could be detected at this stage.

In order to isolate the clone containing the CDNA encoding the mature dog lipase, an additional technique was used.

An mRNA fraction derived from the starting preparation is converted into single-stranded CDNA by means of the enzyme reverse transcriptase and an oligonucleotide primer DPL2 (FIG. 2B) obtained from the 31 terminal sequence of the CDNA contained in the clone 3.12 previously isolated and sequenced.

The CDNA encoding the mature part of the DGL is then obtained and amplified by the PCR method, in the presence of Taq Polymerase and two oligonucleotide primers, DPL2 as mentioned above, and DGL, designed from comparison of the 51 terminal nucleotide sequences of human and rabbit gastric lipases, of rat lingual lipase and of the known $NH_1$-terminal protein sequence of DGL.

The double-stranded CDNA thus obtained was introduced into the vector pbluescript KS(+) after certain modifications and the recombinant molecules were used to transform the bacterium E. coli MM294. The transformant clones were screened by PCR using oligonucleotide probes corresponding to the parts of the sequence of the vector pbluescript KS(+) situated on either side of the insert. The clone PKSPCR containing an insert of 700 base pairs was selected and sequenced.

At the same time, after digestion with the restriction enzyme PstI, the "H" fragment of the CDNA insert of the clone 3.12 as obtained earlier is inserted into the plasmid PKSPCR linearized with PstI; a clone PKSPCR 10 is obtained which contains . the CDNA encoding the mature dog gastric lipase.

Analysis of the nucleotide sequence of this CDNA made it possible to detect an open reading frame of 1137 nucleotides (NT) corresponding to a protein of 379 AA and a molecular weight of 43222 daltons.

Comparison with the nucleotide sequences of the other preduodenal lipases (Docherty, A. P. J. et al. (1985) op. cit.; Bodmer, M. W. et al. (1987) op. cit.; Moreau, E. et al. (1988) op. cit.) reveals a homology of 84.7% with HGL, and of 75.7% with RATLL and 81% with RGL in the coding regions.

Alternatively, a second process can be used for the production of a clone containing the CDNA encoding the mature DGL.

In the case where the mRNAs extracted from dog stomach mucosa, isolated by affinity chromatography on an oligo-dT column, and converted into CDNA by virtue of the use of specific enzymes (Rous Sarcoma Virus reverse transcriptase and E. coli DNA polymerase I) correspond to the whole MRNA of the mature DGL or its precursor, it will be possible to introduce the CDNA thus obtained after certain modifications in the vector pUC18 and the recombinant molecules used to transform a host cell, preferably bacterium or yeast; the transformant clones will be screened by in situ hybridization using probes derived from rabbit gastric lipase.

After autoradiography, the colonies of host cells corresponding to a positive signal during the hybridization will be isolated and the plasmid DNA present in the cytoplasm of these cells amplified and purified. Advantageously, the general cloning techniques used in this second process will be the same as those used in the process described earlier.
General cloning techniques:

The conventional molecular biology methods such as purification of the messenger RNAS, the extraction and purification of plasmid DNA, the. digestion with restriction enzymes, electrophoresis on agarose or polyacrylamide gel, electroelution from agarose gel of DNA fragments, transformation in E. coli, are described in the literature (Maniatis, T. et al., "Molecular cloning: a laboratory manual, Second Edition", Cold Spring Harbor Laboratory, Cold Spring Harbor, N.Y., 1989; Ausubel, F. M. et al. (eds.), "Current Protocols in Molecular Biology", John Willey and Sons, New York, 1987).

The "random priming" is performed according to the method described by Feinberg and Wogelstein (Anal. Biochem. (1983) 132: 6; Anal. Biochem. (1984) 137: 266).

The enzymes are obtained from the Companies Boehringer or New England Biolabs and used under the conditions recommended by the suppliers.

The DNA fragments intended to be assembled are separated according to their size by electrophoresis on 1% agarose gel, purified by electroelution and precipitated with ethanol. The ligation of the DNA fragments is carried out in the presence of T4 DNA ligase at 4° C. or at 16° C. in an appropriate buffer according to whether the pieces to be assembled possess blunt or cohesive ends.

The sequencing of the DNA is carried out according to the dideoxynucleotide method (Sanger, F. et al., Proc. Natl. Acad. Sci. USA. 74 (1977) (5463–5467) using a "T7 sequencing" kit (Pharmacia).

The enzymatic amplification of specific DNA fragments is carried out according to the "Polymerase-catalysed Chain Reaction" or PCR method (Saiki, R. K. et al., Science 220 (19835) 1350-;1354) using a PREM III LEP Scientific apparatus.

The oligonucleotides used as primers in the PCR or sequencing reactions are synthesized using a PCR-MATE Model 391 DNA synthesizer (Applied Biosystems) and purified by high-performance liquid chromatography before they are used.

The recombinant DNA molecules are used to transform competent cells of the following strains of E. coli:

MM294 [F-, endal, hsdRl7 (rk–mk+) I supE44, thi-1, relAll, or

W3110 Iq[F'TraD36, LaCIq, –(lac Z)MLS, pro+]

The plasmid DNA is extracted from the bacterial transformants resistant to ampicillin according to a procedure derived from the alkaline lyse method described by Birnboin and Doly (Birnboim, H. C. and Doly, J., Nucl. Ac. Res. 7 (1979) 1512–1523).

The immunodetection of the dog gastric lipase synthesized in the bacterium E. coli W3110 q, after addition of IsoPropylThioGalactopyranoside (IPTG) to the culture medium, is carried out by an immunoblotting method onto nylon membrane using an anti-DGL guinea-pig antibody and the kit for revealing with ImmunoPure ABC peroxidase (Pierce).

The preparation of the DGL is advantageously illustrated, although with no limitation being implied, by the following example of expression of DGL in the bacterium E. coli W3110 q.

The process for the preparation of the lipase comprises several steps which are detailed in the following text:

Step No. 1: Cloning of a CDNA encoding dog gastric lipase.

1.1. Isolation and purification of the messenger RNAs from dog stomach fundic mucosa.

After grinding the tissues in a buffer containing lithium chloride and urea (Auffray, C. and Rougeon, F., Eur. J. Biochem. 107 (1980) 303–314), the total RNA is separated from the DNA by selective precipitation with lithium chloride. The proteins contaminating the RNA are then removed by phenol extraction. The messenger RNAS, polyadenylated at their 3'OH end, are separated from the ribosomal RNAs by chromatography on an oligo-dt cellulose column (Maniatis, T. et al., already cited). 75 micrograms of messenger RNA are thus obtained per gram of tissue.

1.2. Detection of the messenger RHA encoding DGL in the messenger RNA preparation extracted from dog stomach fundic mucosa.

The dog gastric lipase was purified to homogeneity and its NH2-terminal polypeptide sequence determined (Carriére F. et al., already cited).

A probe consisting of the DNA encoding the rabbit lipase precursor is used to verify the presence of an mRNA encoding DGL in the preparation obtained.

A "Northern" type hybridization experiment is carried out. A sample of 20 gg of dog stomach messenger RNA is denatured at 60*C, in the presence of glyoxal and DMSO, and then the mRNAs are separated according to size, by electrophoresis, on a 1% agarose gel in 10 niM phosphate buffer pH7 (Thomas, P., Proc. Natl. Acad. Sci. USA, 77 (1980) 5201–5205).

After electrophoresis, the messenger RNA is transferred onto nylon membrane (Biodyne PALL) according to the procedure recommended by the supplier.

The cDNA fragment corresponding to the rabbit lipase is labeled by "random priming". The membranes previously obtained are hybridized individually for 36 hours at 37° C. in a 5× SSC buffer –5× Denhardt—50 mm sodium phosphate, pH 6.5— 0.1% SDS—50% formamide, containing 10 ng/ml of the radioactive probe (Ausubel, F. et al. (eds), already cited). The temperatures used take into account the possible sequence homologies between RGL and DGL. An MRNA of about 1700 nucleotides hybridizes with the radioactive probe.

1.3. Synthesis of complementary DNA from dog stomach MRNA and insertion into the vector pUC18.

The synthesis of double-stranded CDNA is carried out starting with 4 gg of polyA+ RNA, in the presence of 50 units of AMV reverse transcriptase, 100 ng of an oligo-dT primer and E. coli DNA polymerase I.

A fraction of this DNA is inserted into the vector pUC18 by means of oligo-dc and oligo-dg tails, which are added respectively onto the CDNA and onto the vector previously linearized with the enzyme PstI (Gubler, U. and Hoffman, B. J., Gene 2–5 (1983) 263–269).

The hybrid molecules are used to transform competent bacteria *E. coli* MM294. The selection of the transformants is carried out by plating the product of the transformation onto a solid nutrient medium (LB-Agar) containing ampicillin at 50 mg/liter.

1.4. Isolation of the cDNA encoding DGL.

The bacterial colonies derived from the transformation are transferred onto nylon membranes (Biodyne PALL) and lysed according to a process recommended by the supplier. The effect of this operation is to denature and to bind onto the membrane the bacterial and plasmid DNA contained in the colonies.

After several washes in a 3× SSC buffer 0.1% SDS, at room temperature and then at 65"C, the filters are prehybridized for two hours at 65° C. in a 6× SSC buffer—10× Denhardt—0.1% SDS, and then hybridized at 50° C. in the same buffer containing the rabbit probe labeled with 32 P by "random priming", at the rate of 0.5 μci per ml of buffer.

The filters are washed in a 2× SSC buffer 0.1% SDS at room temperature then at 50° C. in the same buffer, before being subjected to autoradiography for 24 to 48 hours.

A screening of the, colonies is carried out on two series of filters with the rabbit probe. The clone 3.12 is thus obtained (FIG. 3).

1.5. Synthesis of CDNA by means of the specific oligonucleotide DPL2 and insertion into the vector pBluescript KS(+).

1.5.a. Synthesis of CDNA by means of the specific oligonucleotide $DPL_2$.

A synthesis of single-stranded CDNA is carried out starting with 5 pg of polyA+ RNA, in the presence of 50 units of AMV reverse transcriptase and 100 ng of a synthetic oligonucleotide DPL2 specific for DGL, and corresponding to the sequence in 3' of the CDNA contained in the clone 3.12 described earlier. After extraction of the solution with phenol-chloroform and precipitation in alcohol, the pellet obtained is dissolved in 20 microliters of distilled water; the single-stranded CDNA in solution is then amplified and converted into doublestranded DNA by the "PCRN" technique by means of the primers DGL, and DPL2 which are presented in FIG. 2B, so as to be cloned into an appropriate vector. The DGL, primer used above consists of a mixture of 12 sequences, each of these sequences corresponding to one of the possible combinations for representation of DGL, taking into account the fact that two T nucleotides can be replaced with one C nucleotide, and that one G nucleotide can be replaced with one T nucleotide or one A nucleotide at the positions indicated below the DGL, primer represented in FIGS. 2A and 2B.

1.5.b. Insertion into the vector pbluescrirt KS(+).

After digestion with the enzyme Pstl, the 700 bp fragment of CDNA is inserted into the vector pBluescript KS(+) digested with the restriction enzymes SmaI and PstI.

The recombinant molecules derived from the ligation are used to transform competent bacteria *E. coli* MM294. The selection of the transformants is carried out by plating the product of the transformation on a solid nutrient medium (LB-Agar) containing ampicillin at 50 mg/liter.

The clone PKSPCR is thus obtained.

1.5.c. Ligation of the "H" fragment of the clone 3.12. into the plasmid PKSPCR.

The clone 3.12 is digested with the restriction enzyme Pstl; the PstI-Pstl "H" fragment of 850 base pairs of the clone 3.12 corresponding to the 31 region of the DGL CDNA is inserted into the plasmid PKSPCR previously linearized with the enzyme PstI.

Figure 4:
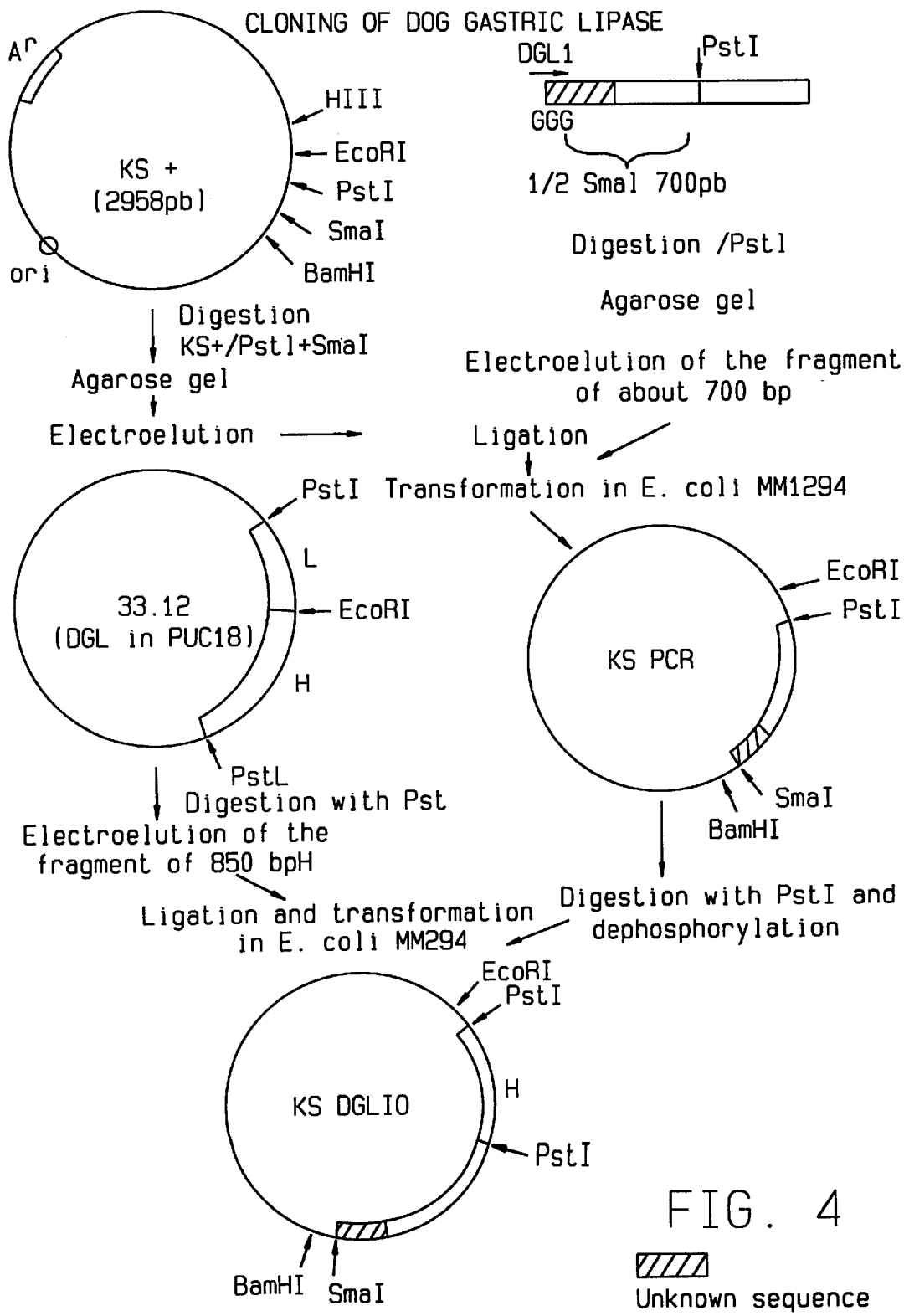
FIG. 4: Scheme for cloning DGL into the vector pBluescript KS(+) and subcloning of the "H" fragment of the clone 3.12. into PKSPCR: production of the clone pKS-DGL10.

The combination of these steps is presented in FIG. 4.

1.6. I-solation of the CDNA from the clone pKS DGL10.

A clone, pKS DGL10, was selected after screening by "PCR" (C. Blanchard and C. Benicourt, *Boehringer*, "Le brin complémentaire", Sep. 1992, No. 8, p6,). The cleavage by restriction enzymes of the plasmid PKSDGLIO shows that it contains a 1.5 Kb insert. This plasmid is prepared from one liter of bacterial culture for its detailed analysis and its sequencing.

The sequencing of the clone is carried out on double-stranded DNA by the Sanger method (Sanger, F. et al., Proc. Natl. Acad. Sci. USA. 74 (1977) 5463–5467).

The complete sequence of the CDNA contains 1528 nucleotides and is presented in FIG. 8. One open reading frame stretching from nucleotide I to nucleotide −1137 encodes a protein of 379 AA. The sequence of this protein is presented in FIG. 9A. This protein has 81% homology with rabbit gastric lipase (French Patent No. 91 13948).

Step No. 2: Construction of plasmids to express DGL in *Escherichia coli*.

2.1. Choice of expression vector.

Figure 5:
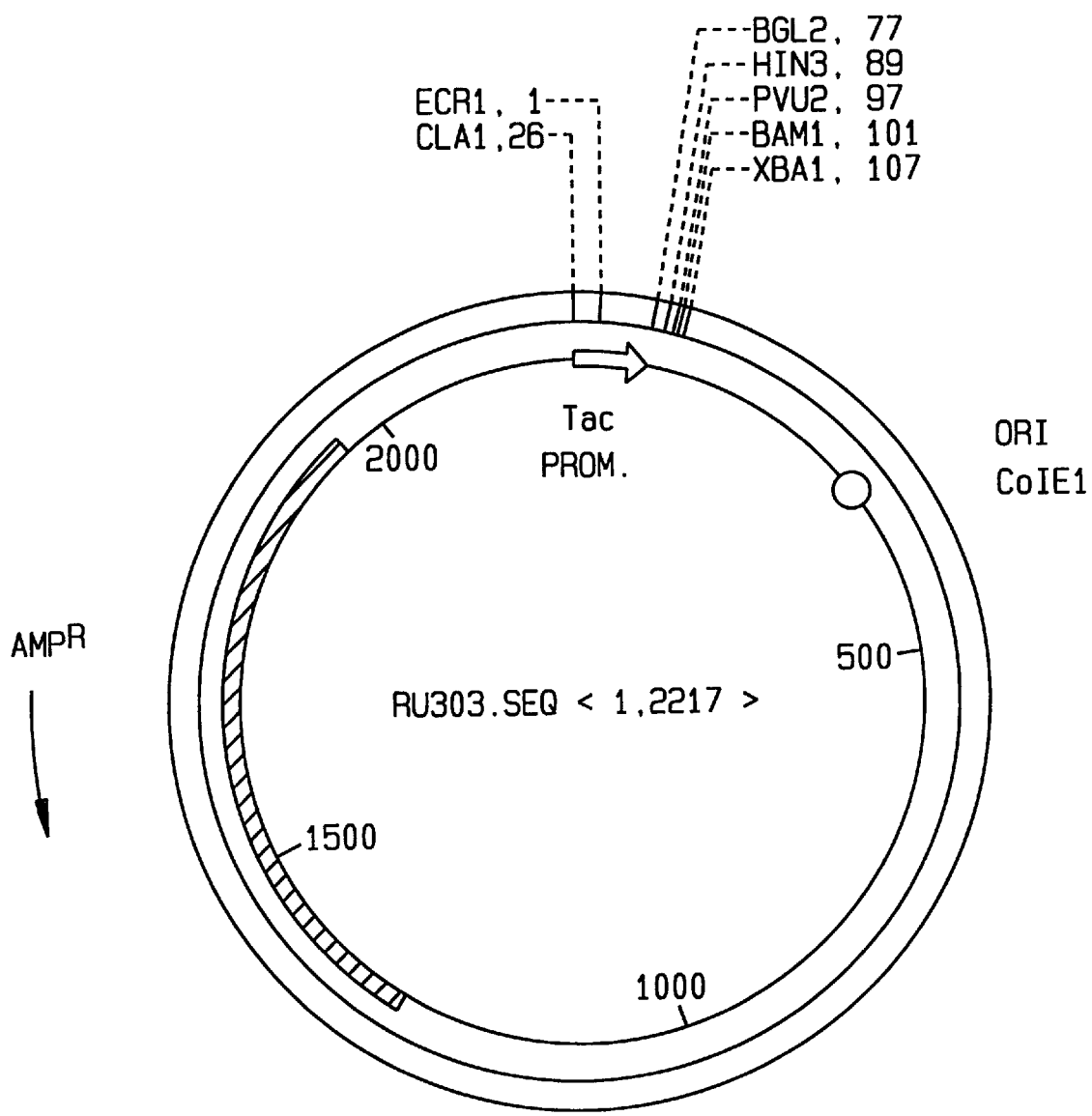
FIG. 5: Restriction map of the plasmid vector pRU303.

The vector chosen to express the DGL in *E. coli* is a plasmid in which a synthetic DNA fragment of 160 bp containing a Tac type promoter and a transcription terminator has been inserted between the EcoRI and NdeI sites of pBR322 (Bolivar, F. et al., Gene 2 (1977) 95–113). The restriction map of the vector pRU303 is presented in FIG. 5 and the nucleotide sequence of the EcoRI-NdeI DNA fragment in FIG. 6.

2.2. Construction of the plasmid pDGL5.303

In spite of exhaustive studies which have been carried out, few correlations have been established between the level of expression of a heterologous protein in a bacterium and the nucleotide sequence of the 51 terminal region of the messenger RNA of this same protein. However, a number of observations have made it possible to deduce certain empirical rules which can result in higher expression levels in the recombinant bacteria.

Among these "rules", there may be mentioned:

the distance between the Shine-Dalgarno region and the initiator AUG between 6 and 12 nucleotides, a Shine-Dalgarno sequence rich in purines (AGGA), a minimum secondary structure between Shine-Dalgarno and initiator AUG, the absence of secondary structure (double strand) in the regions of messenger RNA containing the Shine-Dalgaro sequence and the initiator AUG.

Such constraints can be taken into account in the analysis programs which make it possible to define the nucleotide sequences of the non-coding 51 regions of the mRNAs capable of resulting in the best levels of expression of particular heterologous proteins, such as DGL in *E. coli*.

Figure 10:
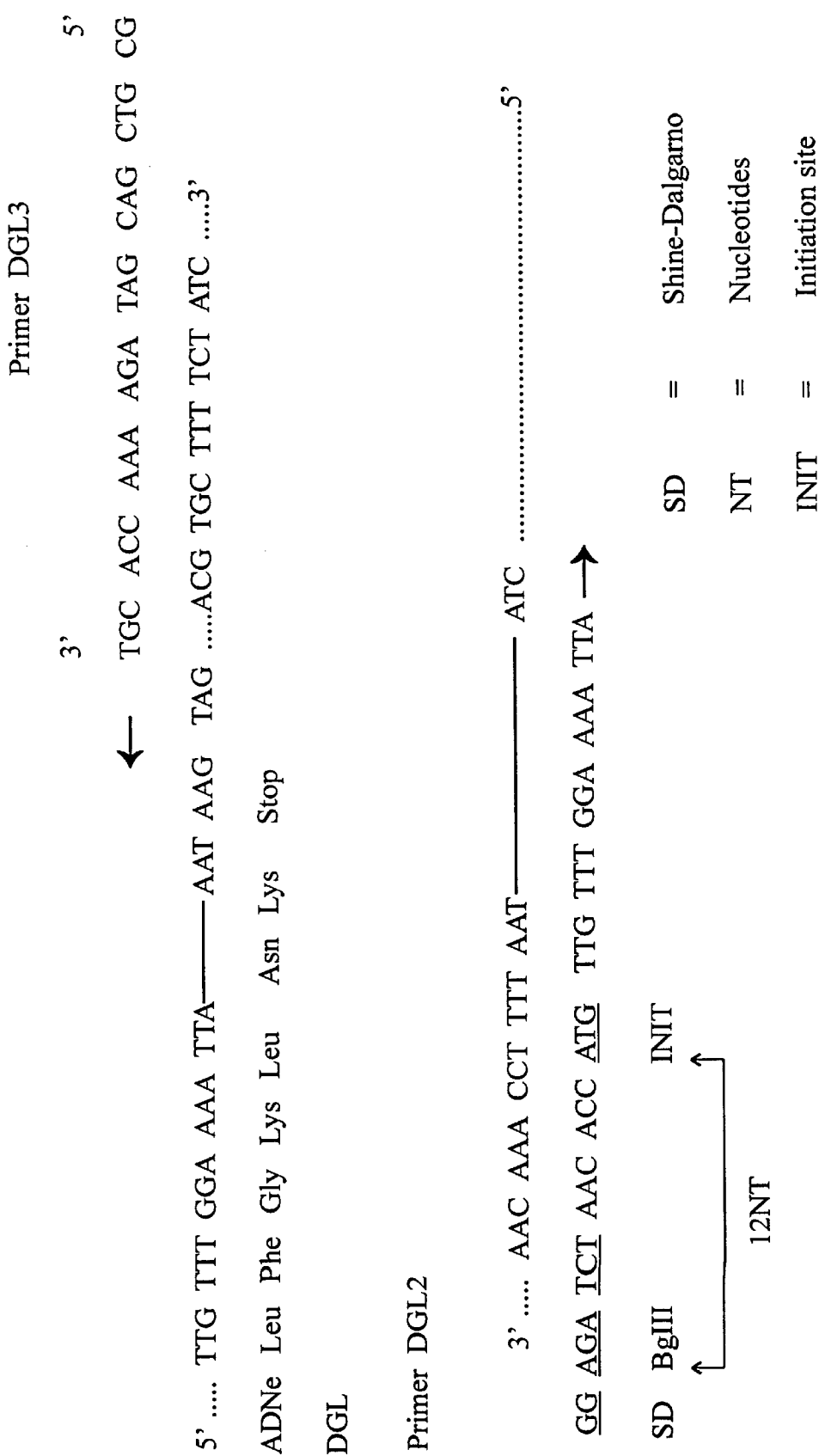
FIG. 10: Mutagenesis in vitro of the CDNA of DGL by the IIPCRI, technique by means of oligonucleotide primers DGL2 (SEQ ID NO 9) and DGL3 (SEQ, ID NO 10) for the construction of the plasmid pDGLS.303.

Using specific synthetic primers DGL2 and DGL3 which are presented in FIG. 10 and the "PCR" gene amplification technique, the CDNA encoding the mature part of DGL is positioned behind an ATG codon for initiation of translation and placed between nucleotide sequences such that it can be inserted into the expression vector pRU303 between the restriction sites BglII and Sall. Because of the presence, in the construct pDGLS.303, of an ATG codon immediately upstream of the sequences encoding DGL, the recombinant proteins obtained will possess, totally or partially, a methionine at their NH2-terminal end.

Figure 7:
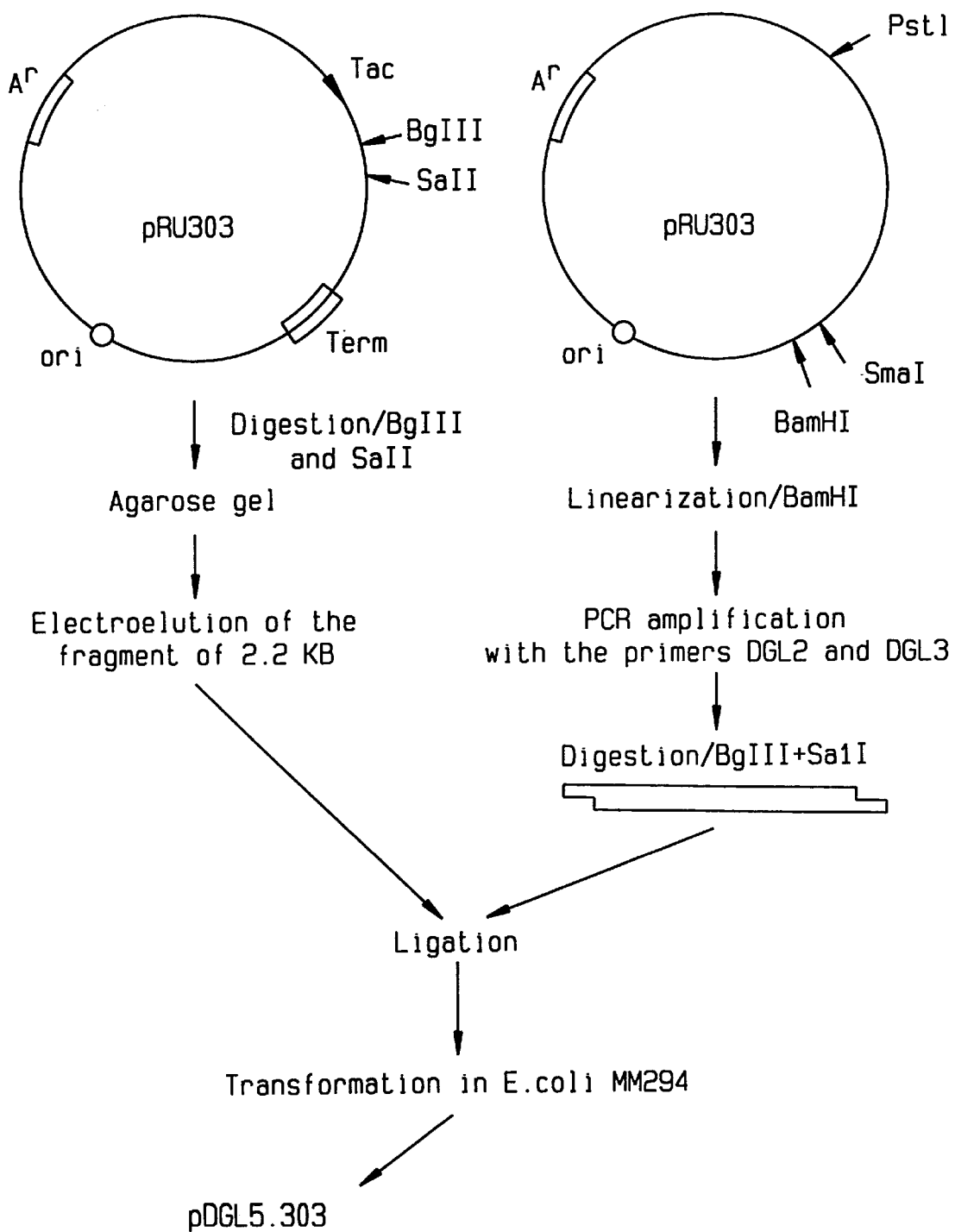
FIG. 7: Subcloning of the CDNA of dog gastric lipase into the expression vector pRU303 and construction of the plasmid pDGL5.303.

The recombinant plasmid pDGL5.303 whose construction scheme is represented in FIG. 7 was obtained in the strain *E. coli* MM294 and then transferred into the strain *E. coli* W3110 Iq, which is frequently used for the expression of heterologous proteins. This strain contains the gene for the repressor LacIl situated on a non-transferable episome F': the repressor synthesized in large quantity in the bacterium represses the expression of all the genes placed under the control of a lactose-type promoter.

Step No. 3: Expression of DGL in E. coli.

The pLasmid pDGLS.303 was introduced into the host E. coli W3110 lq. The bacteria transformed by the plasmid are cultured in medium in the presence of M9 glucose [sic] (Maniatio, T. et al., already cited). During the exponential growth phase, the expression of the dog gastric lipase is induced by addition of IPTG at the final concentration of 2 mM.

After 4 hours at 37° C., the bacteria are harvested, centrifuged and washed with PBS buffer. The bacteria are then lysed in a buffer-containing SDS and P-mercaptoethanol for 10 minutes at 100° C.

Figure 11:
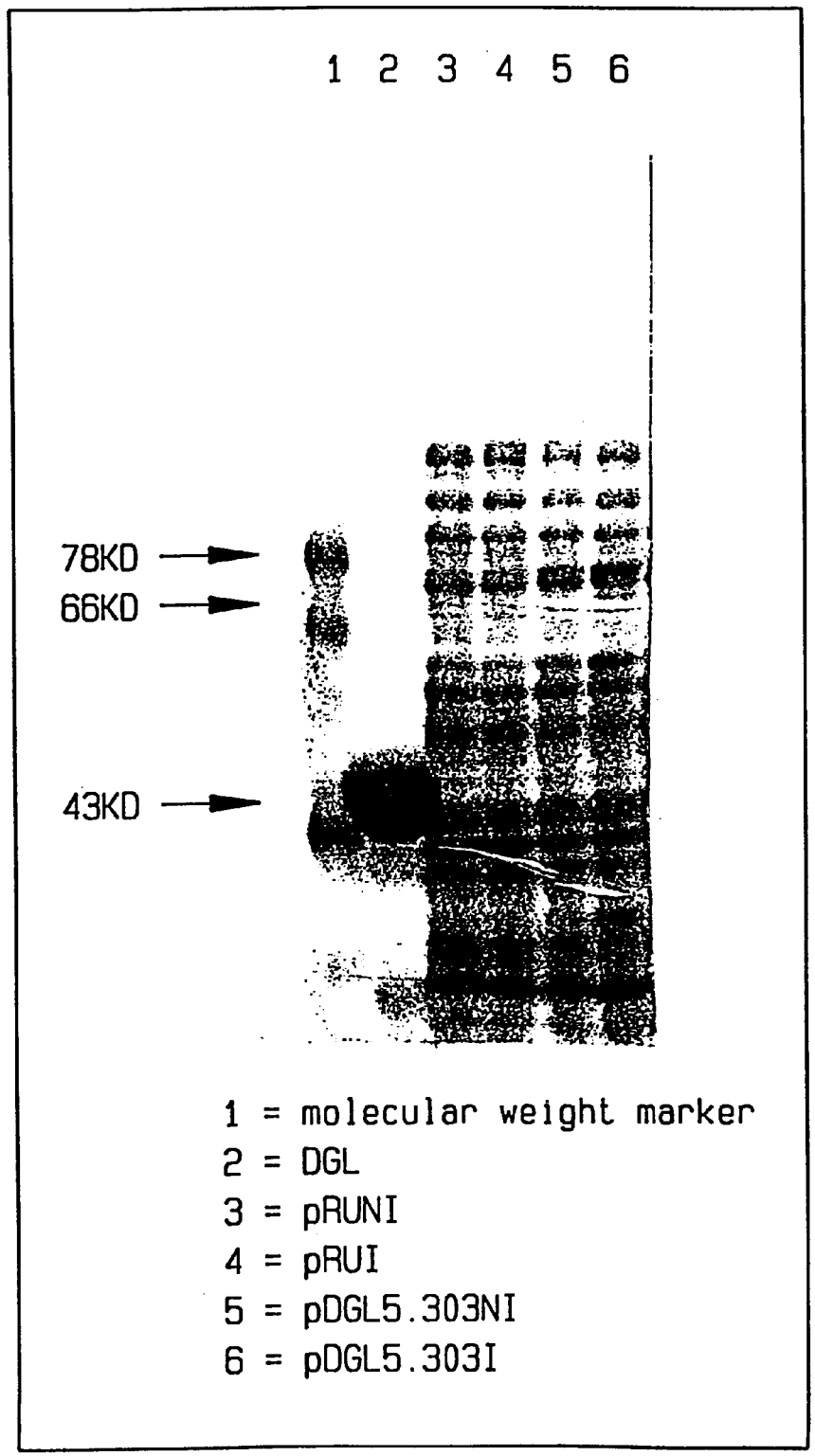
FIG. 11: Analysis by SDS-polyacrylamide gel electrophoresis of the proteins synthesized, in the absence or in the presence of IPTG, in E. coli W3110 Iq transformed with the plasmid pDGL5.303.

Analysis of the proteins on electrophoresis gel under denaturing conditions makes it possible to detect a protein band which may correspond to the lipase. The protein. is expressed at a level such that it can be detected by this technique as shown in FIG. 11.

In order to ensure that this protein, which is induced by the addition of IPTG to the culture medium, indeed corresponds to the DGL, the proteins derived from cultures of bacteria transformed by the plasmid pLGCS.303, induced and non-induced by the chemical agent, are transferred onto a nylon membrane after they have been separated according to their size by SDS-polyacrylamide gel electrophoresis.

Figure 12:
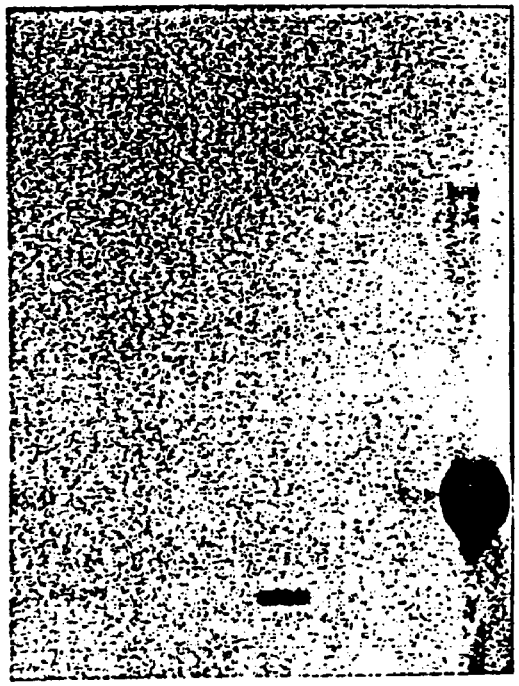
FIG. 12: Immunodetection by means of specific antibodies of the DGL synthesized in E. coli W3110 Iq transformed with the plasmid pDGL5.303 after "Western" type transfer onto nylon membrane of the proteins derived from these bacteria.

The complex between the DGL and the anti-DGL antibody can be detected by means of a calorimetric reaction involving a second antibody coupled to an enzyme, horseradish peroxidase. The results are presented in FIG. 12.

Rather than being produced in the form of inclusion bodies in the cytoplasm of the bacterium Escherichia coli, dog gastric lipase can. be advantageously secreted into the bacterial periplasm by inserting the mature enzyme-encoding CDNA into an appropriate vector, under the control of an inducible promoter by a physical or chemical agent, and downstream of a DNA segment encoding a signal peptide such as that present at the $NH_2$ terminal end of the protein ompA (Movva N. R. et al. J. Biol. Chem. 256: 27–29, 1980).

Dog gastric lipase can also be synthesized in Escherichia coli in the form of a soluble fusion protein with Staphylococcus aureus protein A permitting its subsequent purification. To this end, the mature lipase-encoding CDNA is inserted into the vector pRIT2T (Nilsson B. et al. EMBO J.4: 1075–1080, 1985) which was previously modified in order to introduce therein a DNA fragment encoding the recognition site Ile-Glu-Gly-Arg for coagulation factor Xa. The fusion protein thus produced can be separated from the other proteins of the cytoplasm of the bacterium by affinity chromatography on an IgG-Sepharose column (Pharmacia). After elution of the collimn, the fusion protein is cleaved by factor Xa. The product of the hydrolysis is again subjected to a chromatography on an IgG-Sepharose column which retains protein A, thus making it possible to obtain the dog gastric lipase in the pure state in soluble form.

It is also possible to obtain dog gastric lipase from mammalian cells in culture. For that, the CDNA encoding the precursor of this lipase should be introduced into an appropriate vector such as the plasmid PCDNAI-Neo (Invitrogen corporation) under the control of the Cytomegalovirus (CMV) promoter, or alternatively the mature lipase-encoding CDNA into the same type of vector, but downstream of a DNA segment encoding the signal peptide of rabbit gastric lipase (Bénicourt C. et al.; French Patent Application no. 2,633,549 cited above). The introduction of such recombinant plasmids into monkey kidney COS-7 cells constitutively expressing the SV40 virus T antigen makes it possible to transiently produce dog gastric lipase in the culture medium in an appreciable quantity. Cell lines constitutively expressing dog gastric lipase can be obtained by introducing one of two recombinant plasmids into hamster ovary cells (CHO) and by exerting a selection pressure with the antibiotic G418 or geneticin due to the presence of a gene for resistance to aminoglycosides such as neomycin on the said plasmids.

The detection of the activity of the recombinant DGL, especially that derived from a bacterial lysate obtained from a culture of W3110 Iq (pDGL5.303), is carried out by the method of Gargouri et al. (Gastroenterology 91 (1986) 265–275) using tributyrin as substrate.

The experimental conditions in which the specific activities of the recombinant polypeptides are determined will be recalled below.

The specific activity is defined as the ratio of the enzymatic activity to the quantity of proteins in the sample expressed in milligrams. The lipase activity is determined by the titrimetric method of Y. Gargouri (previously cited) in which the substrate used is tributyrin. The assay consists in neutralizing the butyric acid liberated under the action of the lipase by a O.IN sodium hydroxide solution at constant pH of 6 and at a temperature of 370C. Under these assay conditions, the enzymatic activity corresponds to the number of micromoles of acid which are liberated in one minute by the action of the product subjected to the assay.

Practically, the assay consists in introducing. into a titration cell thermostated at 37° C.:

Tributyrin: 0.50 ml,

Isotonic solution of bovine serum albumin and sodium taurodeoxycholate 14.50 ml (composition: 100 mg bovine serum albumin, 2 mM sodium taurodeoxycholate, 0.9% isotonic solution of NaCl q.s. one liter).

With electromagnetic stirring and with the aid of an automated titrimeter, the mixture is adjusted to pH 6 by addition of 0.1 N sodium hydroxide. After stabilization of the pH at this value, 0.5 to 1 ml of an aqueous solution of the enzymatic compound to be assayed, exactly measured, is added. Under these experimental conditions, the quantity of 0.1 N sodium hydroxide solution necessary to maintain the pH at 6 for 2 minuses makes it possible to calculate the lipase activity as defined earlier.

The lipolytic activity can also be measured by the method using a chromogenic substrate such as resorufin 1,2-0-dilauryl-rac-glycero-3-glutarate (Boehringer), which is described in the manufacturer's leaflet.

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
       (A) LENGTH: 1528 base pairs
       (B) TYPE: nucleic acid
       (C) STRANDEDNESS: double
       (D) TOPOLOGY: linear (ii) MOLECULE TYPE: cDNA to mRNA (xi) SEQUENCE DESCRIPTION: SEQ ID NO: 1:

```
TTGTTTGGAA AATTACATCC CACAAACCCT GAAGTGACCA TGAATATAAG TCAGATGATC    60
ACCTACTGGG GATACCCAGC TGAGGAATAT GAAGTTGTGA CCGAAGACGG TTATATCCTT   120
GGGATCGACA GAATTCCTTA TGGGAGGAAA AATTCAGAGA ATATAGGCCG GAGACCTGTT   180
GCATTTTTGC AACACGGTTT GCTCGCATCA GCCACAAACT GGATCTCCAA CCTGCCCAAC   240
AACAGCCTGG CCTTCATCCT GGCCGACGCC GGGTACGACG TGTGGCTGGG GAACAGCAGG   300
GGCAACACCT GGGCCAGGAG GAATCTGTAC TACTCGCCCG ACTCCGTCGA ATTCTGGGCT   360
TTCAGCTTTG ACGAGATGGC TAAATATGAC CTTCCCGCCA CCATTGACTT CATCTTGAAG   420
AAAACGGGAC AGGACAAGCT ACACTACGTT GGCCATTCCC AGGGCACCAC CATTGGTTTC   480
ATCGCCTTTT CCACCAATCC CAAGCTGGCG AAACGGATCA AAACCTTCTA TGCATTAGCT   540
CCCGTTGCCA CCGTGAAGTA CACCGAAACC CTGTTAAACA AACTCATGCT CGTCCCTTCG   600
TTCCTCTTCA AGCTTATATT TGGAAACAAA ATATTCTACC CACACCACTT CTTTGATCAA   660
TTTCTCGCCA CCGAGGTATG CTCCCGCGAG ACGGTGGATC TCCTCTGCAG CAACGCCCTG   720
TTTATCATTT GTGGATTTGA CACTATGAAC TTGAACATGA GTCGCTTGGA TGTGTATCTG   780
TCACATAATC CAGCAGGAAC ATCGGTTCAG AACGTGCTCC ACTGGTCCCA GGCTGTTAAG   840
TCTGGGAAGT TCCAAGCTTT TGACTGGGGA AGCCCAGTTC AGAACATGAT GCACTATCAT   900
CAGAGCATGC CTCCCTACTA CAACCTGACA GACATGCATG TGCCAATCGC AGTGTGGAAC   960
GGTGGCAACG ACTTGCTGGC CGACCCTCAC GATGTTGACC TTTTGCTTTC CAAGCTCCCC  1020
AATCTCATTT ACCACAGGAA GATTCCTCCT TACAATCACT TGGACTTTAT CTGGGCCATG  1080
GATGCCCCTC AAGCGGTTTA CAATGAAATT GTTTCCATGA TGGGAACAGA TAATAAGTAG  1140
TTCTAGATTT AAGGAATTAT TCTTTTATTG TTCCAAAATA CGTTCTTCTC TCACACGTGG  1200
TTTTCTATCA TGTTTGAGAC ACGGTGATTG TTCCCATGGT TTTGATTTCA GAAATGTGTT  1260
AGCATCAACA ATCTTTCCAT TGGTAATTTT TGAATTTAAA ATGATTTTTA AATTTGGGGC  1320
ATCTGGGTGG CTCAGTTGGC TAAGTCGTCT GCCTTGGCTT AAGTCATGAT CTCGGGGTCC  1380
TAGGATGGAG CCTTGTGTCT GGGCTCCTGC CGGGGCGGGG GTCTGCTTCT CCTCCTGCTG  1440
CTCCCCCCTG CTGCTGTGTG CACACACGCT CTCTCTCTCT CAAATAAATA AATAAATAAA  1500
TACTTAATAA AATAAAAAAA AAAAAAAA                                    1528
```

(2) INFORMATION FOR SEQ ID NO: 2:

(i) SEQUENCE CHARACTERISTICS:
       (A) LENGTH: 1137 base pairs
       (B) TYPE: nucleic acid
       (C) STRANDEDNESS: double
       (D) TOPOLOGY: linear (ii) MOLECULE TYPE: cDNA to mRNA (ix) FEATURE:
    (A) NAME/KEY: CDS
    (B) LOCATION: 1..1137

(xi) SEQUENCE DESCRIPTION: SEQ ID NO: 2:

```
TTG TTT GGA AAA TTA CAT CCC ACA AAC CCT GAA GTG ACC ATG AAT ATA      48
Leu Phe Gly Lys Leu His Pro Thr Asn Pro Glu Val Thr Met Asn Ile
 1               5                  10                  15

AGT CAG ATG ATC ACC TAC TGG GGA TAC CCA GCT GAG GAA TAT GAA GTT      96
Ser Gln Met Ile Thr Tyr Trp Gly Tyr Pro Ala Glu Glu Tyr Glu Val
             20                  25                  30

GTG ACC GAA GAC GGT TAT ATC CTT GGG ATC GAC AGA ATT CCT TAT GGG     144
Val Thr Glu Asp Gly Tyr Ile Leu Gly Ile Asp Arg Ile Pro Tyr Gly
         35                  40                  45

AGG AAA AAT TCA GAG AAT ATA GGC CGG AGA CCT GTT GCA TTT TTG CAA     192
Arg Lys Asn Ser Glu Asn Ile Gly Arg Arg Pro Val Ala Phe Leu Gln
     50                  55                  60

CAC GGT TTG CTC GCA TCA GCC ACA AAC TGG ATC TCC AAC CTG CCC AAC     240
His Gly Leu Leu Ala Ser Ala Thr Asn Trp Ile Ser Asn Leu Pro Asn
 65                  70                  75                  80

AAC AGC CTG GCC TTC ATC CTG GCC GAC GCC GGG TAC GAC GTG TGG CTG     288
Asn Ser Leu Ala Phe Ile Leu Ala Asp Ala Gly Tyr Asp Val Trp Leu
                 85                  90                  95

GGG AAC AGC AGG GGC AAC ACC TGG GCC AGG AGG AAT CTG TAC TAC TCG     336
Gly Asn Ser Arg Gly Asn Thr Trp Ala Arg Arg Asn Leu Tyr Tyr Ser
            100                 105                 110

CCC GAC TCC GTC GAA TTC TGG GCT TTC AGC TTT GAC GAG ATG GCT AAA     384
Pro Asp Ser Val Glu Phe Trp Ala Phe Ser Phe Asp Glu Met Ala Lys
        115                 120                 125

TAT GAC CTT CCC GCC ACC ATT GAC TTC ATC TTG AAG AAA ACG GGA CAG     432
Tyr Asp Leu Pro Ala Thr Ile Asp Phe Ile Leu Lys Lys Thr Gly Gln
    130                 135                 140

GAC AAG CTA CAC TAC GTT GGC CAT TCC CAG GGC ACC ACC ATT GGT TTC     480
Asp Lys Leu His Tyr Val Gly His Ser Gln Gly Thr Thr Ile Gly Phe
145                 150                 155                 160

ATC GCC TTT TCC ACC AAT CCC AAG CTG GCG AAA CGG ATC AAA ACC TTC     528
Ile Ala Phe Ser Thr Asn Pro Lys Leu Ala Lys Arg Ile Lys Thr Phe
                165                 170                 175

TAT GCA TTA GCT CCC GTT GCC ACC GTG AAG TAC ACC GAA ACC CTG TTA     576
Tyr Ala Leu Ala Pro Val Ala Thr Val Lys Tyr Thr Glu Thr Leu Leu
            180                 185                 190

AAC AAA CTC ATG CTC GTC CCT TCG TTC CTC TTC AAG CTT ATA TTT GGA     624
Asn Lys Leu Met Leu Val Pro Ser Phe Leu Phe Lys Leu Ile Phe Gly
        195                 200                 205

AAC AAA ATA TTC TAC CCA CAC CAC TTC TTT GAT CAA TTT CTC GCC ACC     672
Asn Lys Ile Phe Tyr Pro His His Phe Phe Asp Gln Phe Leu Ala Thr
    210                 215                 220

GAG GTA TGC TCC CGC GAG ACG GTG GAT CTC CTC TGC AGC AAC GCC CTG     720
Glu Val Cys Ser Arg Glu Thr Val Asp Leu Leu Cys Ser Asn Ala Leu
225                 230                 235                 240

TTT ATC ATT TGT GGA TTT GAC ACT ATG AAC TTG AAC ATG AGT CGC TTG     768
Phe Ile Ile Cys Gly Phe Asp Thr Met Asn Leu Asn Met Ser Arg Leu
                245                 250                 255

GAT GTG TAT CTG TCA CAT AAT CCA GCA GGA ACA TCG GTT CAG AAC GTG     816
Asp Val Tyr Leu Ser His Asn Pro Ala Gly Thr Ser Val Gln Asn Val
            260                 265                 270

CTC CAC TGG TCC CAG GCT GTT AAG TCT GGG AAG TTC CAA GCT TTT GAC     864
Leu His Trp Ser Gln Ala Val Lys Ser Gly Lys Phe Gln Ala Phe Asp
        275                 280                 285
```

-continued

```
TGG GGA AGC CCA GTT CAG AAC ATG ATG CAC TAT CAT CAG AGC ATG CCT        912
Trp Gly Ser Pro Val Gln Asn Met Met His Tyr His Gln Ser Met Pro
    290                 295                 300

CCC TAC TAC AAC CTG ACA GAC ATG CAT GTG CCA ATC GCA GTG TGG AAC        960
Pro Tyr Tyr Asn Leu Thr Asp Met His Val Pro Ile Ala Val Trp Asn
305                 310                 315                 320

GGT GGC AAC GAC TTG CTG GCC GAC CCT CAC GAT GTT GAC CTT TTG CTT       1008
Gly Gly Asn Asp Leu Leu Ala Asp Pro His Asp Val Asp Leu Leu Leu
                325                 330                 335

TCC AAG CTC CCC AAT CTC ATT TAC CAC AGG AAG ATT CCT CCT TAC AAT       1056
Ser Lys Leu Pro Asn Leu Ile Tyr His Arg Lys Ile Pro Pro Tyr Asn
        340                 345                 350

CAC TTG GAC TTT ATC TGG GCC ATG GAT GCC CCT CAA GCG GTT TAC AAT       1104
His Leu Asp Phe Ile Trp Ala Met Asp Ala Pro Gln Ala Val Tyr Asn
            355                 360                 365

GAA ATT GTT TCC ATG ATG GGA ACA GAT AAT AAG                           1137
Glu Ile Val Ser Met Met Gly Thr Asp Asn Lys
370                 375
```

(2) INFORMATION FOR SEQ ID NO: 3:

(i) SEQUENCE CHARACTERISTICS:
        (A) LENGTH: 379 amino acids
        (B) TYPE: amino acid
        (D) TOPOLOGY: linear (ii) MOLECULE TYPE: protein (xi) SEQUENCE DESCRIPTION: SEQ ID NO: 3:

```
Leu Phe Gly Lys Leu His Pro Thr Asn Pro Glu Val Thr Met Asn Ile
1               5                   10                  15

Ser Gln Met Ile Thr Tyr Trp Gly Tyr Pro Ala Glu Tyr Glu Val
                20                  25                  30

Val Thr Glu Asp Gly Tyr Ile Leu Gly Ile Asp Arg Ile Pro Tyr Gly
            35                  40                  45

Arg Lys Asn Ser Glu Asn Ile Gly Arg Arg Pro Val Ala Phe Leu Gln
        50                  55                  60

His Gly Leu Leu Ala Ser Ala Thr Asn Trp Ile Ser Asn Leu Pro Asn
65              70                  75                  80

Asn Ser Leu Ala Phe Ile Leu Ala Asp Ala Gly Tyr Asp Val Trp Leu
                85                  90                  95

Gly Asn Ser Arg Gly Asn Thr Trp Ala Arg Arg Asn Leu Tyr Tyr Ser
                100                 105                 110

Pro Asp Ser Val Glu Phe Trp Ala Phe Ser Phe Asp Glu Met Ala Lys
            115                 120                 125

Tyr Asp Leu Pro Ala Thr Ile Asp Phe Ile Leu Lys Lys Thr Gly Gln
        130                 135                 140

Asp Lys Leu His Tyr Val Gly His Ser Gln Gly Thr Thr Ile Gly Phe
145             150                 155                 160

Ile Ala Phe Ser Thr Asn Pro Lys Leu Ala Lys Arg Ile Lys Thr Phe
                165                 170                 175

Tyr Ala Leu Ala Pro Val Ala Thr Val Lys Tyr Thr Glu Thr Leu Leu
            180                 185                 190

Asn Lys Leu Met Leu Val Pro Ser Phe Leu Phe Lys Leu Ile Phe Gly
        195                 200                 205

Asn Lys Ile Phe Tyr Pro His His Phe Asp Gln Phe Leu Ala Thr
    210                 215                 220

Glu Val Cys Ser Arg Glu Thr Val Asp Leu Leu Cys Ser Asn Ala Leu
```

```
             225                 230                 235                 240
    Phe Ile Ile Cys Gly Phe Asp Thr Met Asn Leu Asn Met Ser Arg Leu
                    245                 250                 255

Asp Val Tyr Leu Ser His Asn Pro Ala Gly Thr Ser Val Gln Asn Val
                260                 265                 270

Leu His Trp Ser Gln Ala Val Lys Ser Gly Lys Phe Gln Ala Phe Asp
                275                 280                 285

Trp Gly Ser Pro Val Gln Asn Met Met His Tyr His Gln Ser Met Pro
        290                 295                 300

Pro Tyr Tyr Asn Leu Thr Asp Met His Val Pro Ile Ala Val Trp Asn
    305                 310                 315                 320

Gly Gly Asn Asp Leu Leu Ala Asp Pro His Asp Val Asp Leu Leu Leu
                    325                 330                 335

Ser Lys Leu Pro Asn Leu Ile Tyr His Arg Lys Ile Pro Pro Tyr Asn
                    340                 345                 350

His Leu Asp Phe Ile Trp Ala Met Asp Ala Pro Gln Ala Val Tyr Asn
                    355                 360                 365

Glu Ile Val Ser Met Met Gly Thr Asp Asn Lys
        370                 375

(2) INFORMATION FOR SEQ ID NO: 4:

(i) SEQUENCE CHARACTERISTICS:
        (A) LENGTH: 1140 base pairs
        (B) TYPE: nucleic acid
        (C) STRANDEDNESS: double
        (D) TOPOLOGY: linear (ii) MOLECULE TYPE: cDNA to mRNA (ix) FEATURE:
         (A) NAME/KEY: CDS
         (B) LOCATION: 1..1140

(xi) SEQUENCE DESCRIPTION: SEQ ID NO: 4:

ATG TTG TTT GGA AAA TTA CAT CCC ACA AAC CCT GAA GTG ACC ATG AAT      48
Met Leu Phe Gly Lys Leu His Pro Thr Asn Pro Glu Val Thr Met Asn
 1               5                  10                  15

ATA AGT CAG ATG ATC ACC TAC TGG GGA TAC CCA GCT GAG GAA TAT GAA      96
Ile Ser Gln Met Ile Thr Tyr Trp Gly Tyr Pro Ala Glu Glu Tyr Glu
                20                  25                  30

GTT GTG ACC GAA GAC GGT TAT ATC CTT GGG ATC GAC AGA ATT CCT TAT     144
Val Val Thr Glu Asp Gly Tyr Ile Leu Gly Ile Asp Arg Ile Pro Tyr
            35                  40                  45

GGG AGG AAA AAT TCA GAG AAT ATA GGC CGG AGA CCT GTT GCA TTT TTG     192
Gly Arg Lys Asn Ser Glu Asn Ile Gly Arg Arg Pro Val Ala Phe Leu
 50                  55                  60

CAA CAC GGT TTG CTC GCA TCA GCC ACA AAC TGG ATC TCC AAC CTG CCC     240
Gln His Gly Leu Leu Ala Ser Ala Thr Asn Trp Ile Ser Asn Leu Pro
 65                  70                  75                  80

AAC AAC AGC CTG GCC TTC ATC CTG GCC GAC GCC GGG TAC GAC GTG TGG     288
Asn Asn Ser Leu Ala Phe Ile Leu Ala Asp Ala Gly Tyr Asp Val Trp
                85                  90                  95

CTG GGG AAC AGC AGG GGC AAC ACC TGG GCC AGG AGG AAT CTG TAC TAC     336
Leu Gly Asn Ser Arg Gly Asn Thr Trp Ala Arg Arg Asn Leu Tyr Tyr
            100                 105                 110

TCG CCC GAC TCC GTC GAA TTC TGG GCT TTC AGC TTT GAC GAG ATG GCT     384
Ser Pro Asp Ser Val Glu Phe Trp Ala Phe Ser Phe Asp Glu Met Ala
        115                 120                 125

AAA TAT GAC CTT CCC GCC ACC ATT GAC TTC ATC TTG AAG AAA ACG GGA     432
Lys Tyr Asp Leu Pro Ala Thr Ile Asp Phe Ile Leu Lys Lys Thr Gly
```

-continued

```
           130                 135                 140
CAG GAC AAG CTA CAC TAC GTT GGC CAT TCC CAG GGC ACC ACC ATT GGT      480
Gln Asp Lys Leu His Tyr Val Gly His Ser Gln Gly Thr Thr Ile Gly
145                 150                 155                 160

TTC ATC GCC TTT TCC ACC AAT CCC AAG CTG GCG AAA CGG ATC AAA ACC      528
Phe Ile Ala Phe Ser Thr Asn Pro Lys Leu Ala Lys Arg Ile Lys Thr
                165                 170                 175

TTC TAT GCA TTA GCT CCC GTT GCC ACC GTG AAG TAC ACC GAA ACC CTG      576
Phe Tyr Ala Leu Ala Pro Val Ala Thr Val Lys Tyr Thr Glu Thr Leu
                180                 185                 190

TTA AAC AAA CTC ATG CTC GTC CCT TCG TTC CTC TTC AAG CTT ATA TTT      624
Leu Asn Lys Leu Met Leu Val Pro Ser Phe Leu Phe Lys Leu Ile Phe
                195                 200                 205

GGA AAC AAA ATA TTC TAC CCA CAC CAC TTC TTT GAT CAA TTT CTC GCC      672
Gly Asn Lys Ile Phe Tyr Pro His His Phe Phe Asp Gln Phe Leu Ala
210                 215                 220

ACC GAG GTA TGC TCC CGC GAG ACG GTG GAT CTC CTC TGC AGC AAC GCC      720
Thr Glu Val Cys Ser Arg Glu Thr Val Asp Leu Leu Cys Ser Asn Ala
225                 230                 235                 240

CTG TTT ATC ATT TGT GGA TTT GAC ACT ATG AAC TTG AAC ATG AGT CGC      768
Leu Phe Ile Ile Cys Gly Phe Asp Thr Met Asn Leu Asn Met Ser Arg
                245                 250                 255

TTG GAT GTG TAT CTG TCA CAT AAT CCA GCA GGA ACA TCG GTT CAG AAC      816
Leu Asp Val Tyr Leu Ser His Asn Pro Ala Gly Thr Ser Val Gln Asn
                260                 265                 270

GTG CTC CAC TGG TCC CAG GCT GTT AAG TCT GGG AAG TTC CAA GCT TTT      864
Val Leu His Trp Ser Gln Ala Val Lys Ser Gly Lys Phe Gln Ala Phe
                275                 280                 285

GAC TGG GGA AGC CCA GTT CAG AAC ATG ATG CAC TAT CAT CAG AGC ATG      912
Asp Trp Gly Ser Pro Val Gln Asn Met Met His Tyr His Gln Ser Met
290                 295                 300

CCT CCC TAC TAC AAC CTG ACA GAC ATG CAT GTG CCA ATC GCA GTG TGG      960
Pro Pro Tyr Tyr Asn Leu Thr Asp Met His Val Pro Ile Ala Val Trp
305                 310                 315                 320

AAC GGT GGC AAC GAC TTG CTG GCC GAC CCT CAC GAT GTT GAC CTT TTG     1008
Asn Gly Gly Asn Asp Leu Leu Ala Asp Pro His Asp Val Asp Leu Leu
                325                 330                 335

CTT TCC AAG CTC CCC AAT CTC ATT TAC CAC AGG AAG ATT CCT CCT TAC     1056
Leu Ser Lys Leu Pro Asn Leu Ile Tyr His Arg Lys Ile Pro Pro Tyr
                340                 345                 350

AAT CAC TTG GAC TTT ATC TGG GCC ATG GAT GCC CCT CAA GCG GTT TAC     1104
Asn His Leu Asp Phe Ile Trp Ala Met Asp Ala Pro Gln Ala Val Tyr
                355                 360                 365

AAT GAA ATT GTT TCC ATG ATG GGA ACA GAT AAT AAG                     1140
Asn Glu Ile Val Ser Met Met Gly Thr Asp Asn Lys
370                 375                 380
```

(2) INFORMATION FOR SEQ ID NO: 5:

(i) SEQUENCE CHARACTERISTICS:
        (A) LENGTH: 380 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Leu Phe Gly Lys Leu His Pro Thr Asn Pro Glu Val Thr Met Asn
 1               5                  10                  15

Ile Ser Gln Met Ile Thr Tyr Trp Gly Tyr Pro Ala Glu Glu Tyr Glu
                20                  25                  30
```

```
Val Val Thr Glu Asp Gly Tyr Ile Leu Gly Ile Asp Arg Ile Pro Tyr
         35                  40                  45
Gly Arg Lys Asn Ser Glu Asn Ile Gly Arg Arg Pro Val Ala Phe Leu
 50                  55                  60
Gln His Gly Leu Leu Ala Ser Ala Thr Asn Trp Ile Ser Asn Leu Pro
 65                  70                  75                  80
Asn Asn Ser Leu Ala Phe Ile Leu Ala Asp Ala Gly Tyr Asp Val Trp
                 85                  90                  95
Leu Gly Asn Ser Arg Gly Asn Thr Trp Ala Arg Arg Asn Leu Tyr Tyr
                100                 105                 110
Ser Pro Asp Ser Val Glu Phe Trp Ala Phe Ser Phe Asp Glu Met Ala
                115                 120                 125
Lys Tyr Asp Leu Pro Ala Thr Ile Asp Phe Ile Leu Lys Lys Thr Gly
130                 135                 140
Gln Asp Lys Leu His Tyr Val Gly His Ser Gln Gly Thr Thr Ile Gly
145                 150                 155                 160
Phe Ile Ala Phe Ser Thr Asn Pro Lys Leu Ala Lys Arg Ile Lys Thr
                165                 170                 175
Phe Tyr Ala Leu Ala Pro Val Ala Thr Val Lys Tyr Thr Glu Thr Leu
                180                 185                 190
Leu Asn Lys Leu Met Leu Val Pro Ser Phe Leu Phe Lys Leu Ile Phe
                195                 200                 205
Gly Asn Lys Ile Phe Tyr Pro His His Phe Phe Asp Gln Phe Leu Ala
210                 215                 220
Thr Glu Val Cys Ser Arg Glu Thr Val Asp Leu Leu Cys Ser Asn Ala
225                 230                 235                 240
Leu Phe Ile Ile Cys Gly Phe Asp Thr Met Asn Leu Asn Met Ser Arg
                245                 250                 255
Leu Asp Val Tyr Leu Ser His Asn Pro Ala Gly Thr Ser Val Gln Asn
                260                 265                 270
Val Leu His Trp Ser Gln Ala Val Lys Ser Gly Lys Phe Gln Ala Phe
                275                 280                 285
Asp Trp Gly Ser Pro Val Gln Asn Met Met His Tyr His Gln Ser Met
                290                 295                 300
Pro Pro Tyr Tyr Asn Leu Thr Asp Met His Val Pro Ile Ala Val Trp
305                 310                 315                 320
Asn Gly Gly Asn Asp Leu Leu Ala Asp Pro His Asp Val Asp Leu Leu
                325                 330                 335
Leu Ser Lys Leu Pro Asn Leu Ile Tyr His Arg Lys Ile Pro Pro Tyr
                340                 345                 350
Asn His Leu Asp Phe Ile Trp Ala Met Asp Ala Pro Gln Ala Val Tyr
                355                 360                 365
Asn Glu Ile Val Ser Met Met Gly Thr Asp Asn Lys
370                 375                 380
```

(2) INFORMATION FOR SEQ ID NO: 6:

(i) SEQUENCE CHARACTERISTICS:
        (A) LENGTH: 1146 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO: 6:

TTGTTTGGAA AATTACATCC CACAAACCCT GAAGTGACCA TGAATATAAG TCAGATGATC    60

```
ACCTACTGGG GATACCCAGC TGAGGAATAT GAAGTTGTGA CCGAAGACGG TTATATCCTT      120

GGGATCGACA GAATTCCTTA TGGGAGGAAA AATTCAGAGA ATATAGGCCG GAGACCTGTT      180

GCATTTTTGC AACACGGTTT GCTCGCATCA GCCACAAACT GGATCTCCAA CCTGCCCAAC      240

AACAGCCTGG CCTTCATCCT GGCCGACGCC GGGTACGACG TGTGGCTGGG AACAGCAGG       300

GGCAACACCT GGGCCAGGAG GAATCTGTAC TACTCGCCCG ACTCCGTCGA ATTCTGGGCT      360

TTCAGCTTTG ACGAGATGGC TAAATATGAC CTTCCCGCCA CCATTGACTT CATCTTGAAG      420

AAAACGGGAC AGGACAAGCT ACACTACGTT GGCCATTCCC AGGGCACCAC CATTGGTTTC      480

ATCGCCTTTT CCACCAATCC CAAGCTGGCG AAACGGATCA AAACCTTCTA TGCATTAGCT      540

CCCGTTGCCA CCGTGAAGTA CACCGAAACC CTGTTAAACA AACTCATGCT CGTCCCTTCG      600

TTCCTCTTCA AGCTTATATT TGGAAACAAA ATATTCTACC CACACCACTT CTTTGATCAA      660

TTTCTCGCCA CCGAGGTATG CTCCCGCGAG ACGGTGGATC TCCTCTGCAG CAACGCCCTG      720

TTTATCATTT GTGGATTTGA CACTATGAAC TTGAACATGA GTCGCTTGGA TGTGTATCTG      780

TCACATAATC CAGCAGGAAC ATCGGTTCAG AACGTGCTCC ACTGGTCCCA GGCTGTTAAG      840

TCTGGGAAGT TCCAAGCTTT TGACTGGGGA AGCCCAGTTC AGAACATGAT GCACTATCAT      900

CAGAGCATGC CTCCCTACTA CAACCTGACA GACATGCATG TGCCAATCGC AGTGTGGAAC      960

GGTGGCAACG ACTTGCTGGC CGACCCTCAC GATGTTGACC TTTTGCTTTC CAAGCTCCCC     1020

AATCTCATTT ACCACAGGAA GATTCCTCCT TACAATCACT TGGACTTTAT CTGGGCCATG     1080

GATGCCCCTC AAGCGGTTTA CAATGAAATT GTTTCCATGA TGGGAACAGA TAATAAGTAG     1140

TTCTAG                                                                1146
```

(2) INFORMATION FOR SEQ ID NO: 7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

```
GGGCACATGG TTTGTTTGGA AAA                                               23
```

(2) INFORMATION FOR SEQ ID NO: 8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

```
ACTACTATCA CGTAGTA                                                      17
```

(2) INFORMATION FOR SEQ ID NO: 9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

GGAGATCTAA CACCATGTTG TTTGGAAAAT TA                               32

(2) INFORMATION FOR SEQ ID NO: 10:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 10:

GCGTCGACGA TAGAAAACCA CGT                                         23

(2) INFORMATION FOR SEQ ID NO: 11:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (xi) SEQUENCE DESCRIPTION: SEQ ID NO: 11:

Leu Phe Gly Lys
1

(2) INFORMATION FOR SEQ ID NO:12:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:12:

Thr His Gly Leu Phe Gly Lys
1               5

(2) INFORMATION FOR SEQ ID NO:13:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:13:

Thr His Gly Leu Phe Gly Lys
1               5

(2) INFORMATION FOR SEQ ID NO:14:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:14:

Ala His Gly Leu Phe Gly Lys
1               5

(2) INFORMATION FOR SEQ ID NO:15:

(i) SEQUENCE CHARACTERISTICS:
        (A) LENGTH: 161 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:15:

```
GAATTCAGTA TTGACAATTT ATACATCGAT ATGGTATAAT GTGTGGAATT GTGAGCGGAT     60
AACAATTTCA CACAGGAGAT CTGCAGGTAA GCTTCAGCTG GGATCCTCTA GAGTCGACGT    120
GAAAAATGGC GCACATTGTG CGACATTTTT TTTGTCATAT G                       161
```

(2) INFORMATION FOR SEQ ID NO:16:

(i) SEQUENCE CHARACTERISTICS:
        (A) LENGTH: 380 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

```
Leu Phe Gly Lys Leu His Pro Gly Ser Pro Glu Val Thr Met Asn Ile
1               5                   10                  15

Ser Gln Met Ile Thr Tyr Trp Gly Tyr Pro Asn Glu Glu Tyr Glu Val
            20                  25                  30

Val Thr Glu Asp Gly Tyr Ile Leu Glu Val Asn Arg Ile Pro Tyr Gly
        35                  40                  45

Lys Lys Asn Ser Gly Asn Thr Gly Gln Arg Pro Val Val Phe Leu Gln
    50                  55                  60

His Gly Leu Leu Ala Ser Ala Thr Asn Trp Ile Ser Asn Leu Pro Asn
65                  70                  75                  80

Asn Ser Leu Ala Phe Ile Leu Ala Asp Ala Gly Tyr Asp Val Trp Leu
                85                  90                  95

Gly Asn Ser Arg Gly Asn Thr Trp Ala Arg Arg Asn Leu Tyr Tyr Ser
            100                 105                 110

Pro Asp Ser Val Glu Phe Trp Ala Ala Phe Ser Phe Asp Glu Met Ala
        115                 120                 125

Lys Tyr Asp Leu Pro Ala Thr Ile Asp Phe Ile Val Lys Lys Thr Gly
    130                 135                 140

Gln Lys Gln Leu His Tyr Val Gly His Ser Gln Gly Thr Thr Ile Gly
145                 150                 155                 160

Phe Ile Ala Phe Ser Thr Asn Pro Ser Leu Ala Lys Arg Ile Lys Thr
                165                 170                 175

Phe Tyr Ala Leu Ala Pro Val Ala Thr Val Lys Tyr Thr Lys Ser Leu
            180                 185                 190

Ile Asn Lys Leu Arg Phe Val Pro Gln Ser Leu Phe Lys Phe Ile Phe
        195                 200                 205

Gly Asp Lys Ile Phe Tyr Pro His Asn Phe Phe Asp Gln Phe Leu Ala
    210                 215                 220

Thr Glu Val Cys Ser Arg Glu Met Leu Asn Leu Cys Ser Asn Ala
225                 230                 235                 240

Leu Phe Ile Ile Cys Gly Phe Asp Ser Lys Asn Phe Asn Thr Ser Arg
                245                 250                 255

Leu Asp Val Tyr Leu Ser His Asn Pro Ala Gly Thr Ser Val Gln Asn
```

```
                    260                 265                 270
Met Phe His Trp Thr Gln Ala Val Lys Ser Gly Lys Phe Gln Ala Tyr
                275                 280                 285
Asp Trp Gly Ser Pro Val Gln Asn Arg Met His Tyr Asp Gln Ser Gln
            290                 295                 300
Pro Pro Tyr Tyr Asn Val Thr Ala Met Asn Val Pro Ile Ala Val Trp
305                 310                 315                 320
Asn Gly Gly Lys Asp Leu Leu Ala Asp Pro Gln Asp Val Gly Leu Leu
                325                 330                 335
Leu Pro Lys Leu Pro Asn Leu Ile Tyr His Lys Glu Ile Pro Phe Tyr
                340                 345                 350
Asn His Leu Asp Phe Ile Trp Ala Met Asp Ala Pro Gln Glu Val Tyr
                355                 360                 365
Asn Asp Ile Val Ser Met Ile Ser Glu Asp Lys Lys
                370                 375                 380
```

(2) INFORMATION FOR SEQ ID NO:17:

(i) SEQUENCE CHARACTERISTICS:
        (A) LENGTH: 377 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

```
Leu Phe Gly Lys Leu Gly Pro Gly Asn Pro Glu Ala Asn Met Asn Ile
1               5                   10                  15
Ser Gln Met Ile Thr Tyr Trp Gly Tyr Pro Cys Gln Glu Tyr Glu Val
                20                  25                  30
Val Thr Glu Asp Gly Tyr Ile Leu Gly Val Tyr Arg Ile Pro His Gly
            35                  40                  45
Lys Asn Asn Ser Glu Asn Ile Gly Lys Arg Pro Val Val Tyr Leu Gln
        50                  55                  60
His Gly Leu Ile Ala Ser Ala Thr Asn Trp Ile Ala Asn Leu Pro Asn
65                  70                  75                  80
Asn Ser Leu Ala Phe Met Leu Ala Asp Ala Gly Tyr Asp Val Trp Leu
                85                  90                  95
Gly Asn Ser Arg Gly Asn Thr Trp Ser Arg Lys Asn Val Tyr Tyr Ser
                100                 105                 110
Pro Asp Ser Val Glu Phe Trp Ala Phe Ser Phe Asp Glu Met Ala Lys
            115                 120                 125
Tyr Asp Leu Pro Ala Thr Ile Asn Phe Ile Val Gln Lys Thr Gly Gln
        130                 135                 140
Glu Lys Ile His Tyr Val Gly His Ser Gln Gly Thr Thr Ile Gly Phe
145                 150                 155                 160
Ile Ala Phe Ser Thr Asn Pro Thr Leu Ala Lys Lys Ile Lys Thr Phe
                165                 170                 175
Tyr Ala Leu Ala Pro Val Ala Thr Val Lys Tyr Thr Gln Ser Pro Leu
                180                 185                 190
Lys Lys Ile Ser Phe Ile Pro Thr Phe Leu Phe Lys Leu Met Phe Gly
            195                 200                 205
Lys Lys Met Phe Leu Pro His Thr Tyr Phe Asp Asp Phe Leu Gly Thr
        210                 215                 220
Glu Val Cys Ser Arg Glu Val Leu Asp Leu Leu Cys Ser Asn Thr Leu
225                 230                 235                 240
```

```
Phe Ile Phe Cys Gly Phe Asp Lys Lys Asn Leu Asn Val Ser Arg Phe
                245                 250                 255

Asp Val Tyr Leu Gly His Asn Pro Ala Gly Thr Ser Val Gln Asp Phe
                260                 265                 270

Leu His Trp Ala Gln Leu Val Arg Ser Gly Lys Phe Gln Ala Phe Asn
                275                 280                 285

Trp Gly Ser Pro Ser Gln Asn Met Leu His Tyr Asn Gln Lys Thr Pro
                290                 295                 300

Pro Glu Tyr Asp Val Ser Ala Met Thr Val Pro Val Ala Val Trp Asn
305                 310                 315                 320

Gly Gly Asn Asp Ile Leu Ala Asp Pro Gln Asp Val Ala Met Leu Leu
                325                 330                 335

Pro Lys Leu Ser Asn Leu Leu Phe His Lys Glu Ile Leu Ala Tyr Asn
                340                 345                 350

His Leu Asp Phe Ile Trp Ala Met Asp Ala Pro Gln Glu Val Tyr Asn
                355                 360                 365

Glu Met Ile Ser Met Met Ala Glu Asp
                370                 375

(2) INFORMATION FOR SEQ ID NO:18:

(i) SEQUENCE CHARACTERISTICS:
        (A) LENGTH: 379 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

Leu Phe Gly Lys Ser Ala Pro Thr Asn Pro Glu Val Asn Met Asn Ile
1               5                   10                  15

Ser Gln Met Ile Ser Tyr Trp Gly Tyr Pro Ser Glu Lys Tyr Glu Val
                20                  25                  30

Val Thr Glu Asp Gly Tyr Ile Leu Glu Val Asn Arg Ile Pro Tyr Gly
                35                  40                  45

Lys Lys Asn Ser Gly Asn Arg Gly Gln Arg Pro Val Val Phe Leu Gln
50                  55                  60

His Gly Leu Leu Ala Ser Ala Ser Asn Trp Ile Ser Asn Leu Pro Asn
65                  70                  75                  80

Asn Ser Leu Ala Phe Ile Leu Ala Asp Ala Gly Tyr Gly Val Trp Leu
                85                  90                  95

Gly Asn Ser Arg Gly Asn Thr Trp Ser Arg Arg Asn Leu Tyr Tyr Ser
                100                 105                 110

Pro Asp Ser Val Glu Phe Trp Ala Phe Ser Phe Asp Glu Met Ala Lys
                115                 120                 125

Tyr Asp Leu Pro Ala Thr Ile Asp Phe Ile Val Lys Glu Thr Gly Gln
                130                 135                 140

Glu Lys Leu His Tyr Val Gly His Ser Gln Gly Thr Thr Ile Gly Phe
145                 150                 155                 160

Ile Ala Phe Ser Thr Asn Pro Lys Leu Ala Glu Arg Ile Lys Thr Phe
                165                 170                 175

Tyr Ala Leu Ala Pro Val Ala Thr Val Lys Tyr Thr Lys Ser Leu Val
                180                 185                 190

Asn Lys Leu Arg Phe Ile Pro Pro Thr Met Phe Lys Ile Ile Phe Gly
                195                 200                 205
```

```
Asp Lys Ile Phe Tyr Pro His Asn Phe Phe Asp Gln Phe Leu Ala Thr
    210                 215                 220

Gln Val Cys Ser Arg Glu Thr Leu Asn Val Ile Cys Ser Asn Ala Leu
225                 230                 235                 240

Phe Ile Ile Cys Gly Phe Asp Ser Ala Asn Leu Asn Met Ser Arg Leu
                245                 250                 255

Asp Val Tyr Val Ser His Asn Pro Ala Gly Thr Ser Val Gln Asn Met
            260                 265                 270

Leu His Trp Thr Gln Ala Val Lys Ser Gly Asn Phe Gln Ala Phe Asn
        275                 280                 285

Trp Gly Ser Pro Ala Gln Asn Val Val His Phe Asn Gln Pro Thr Pro
290                 295                 300

Pro Tyr Tyr Asn Val Thr Ala Met Asn Val Pro Ile Ala Val Trp Ser
305                 310                 315                 320

Gly Gly Asn Asp Trp Leu Ala Asp Pro Gln Asp Val Asp Leu Leu Leu
                325                 330                 335

Pro Lys Leu Ser Asn Leu Ile Tyr His Lys Glu Ile Leu Pro Tyr Asn
            340                 345                 350

His Leu Asp Phe Ile Trp Ala Met Asn Ala Pro Gln Glu Val Tyr Asn
        355                 360                 365

Glu Ile Ile Ser Met Met Ala Lys Asp Lys Lys
370                 375

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

CACATGGTTT GTTTGGAAAA                                                    20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

CACATGGTCT TTTGGAAAA                                                     20

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

CACATGGCCT ATTTGGAAAA                                                    20
```

What is claimed is: 1. A purified polypeptide that is encoded by the nucleic acid sequence of SEQ ID NO 1 or SEQ ID NO 2.

2. Pharmaceutical composition characterized in that it comprises at least one polypeptide according to claim 1, optionally in combination with one or several other polypeptides with lipase activity, or with a pharmaceutically acceptable vehicle.

3. A purified polypeptide comprising SEQ ID NO 3.

4. Pharmaceutical composition characterized in that it comprises at least one polypeptide according to claim 3, optionally in combination with one or several other polypeptides with lipase activity, or with a pharmaceutically acceptable vehicle.

5. A purified polypeptide comprising SEQ ID NO 5.

6. Pharmaceutical composition characterized in that it comprises at least one polypeptide according to claim 5, optionally in combination with one or several other polypeptides with lipase activity, or with a pharmaceutically acceptable vehicle.

* * * * *